United States Patent
Nirogi et al.

(10) Patent No.: US 12,122,779 B2
(45) Date of Patent: Oct. 22, 2024

(54) PYRROLO-PYRIDAZINE DERIVATIVES AS MUSCARINIC M1 RECEPTOR POSITIVE ALLOSTERIC MODULATORS

(71) Applicant: SUVEN LIFE SCIENCES LIMITED, Hyderabad-Telangana (IN)

(72) Inventors: Ramakrishna Nirogi, Hyderabad (IN); Abdul Rashee Mohammed, Hyderabad (IN); Anil Karbhari Shinde, Hyderabad (IN); Srinivasa Rao Ravella, Hyderabad (IN); Ramkumar Subramanian, Hyderabad (IN); Venkateswarlu Jasti, Hyderabad (IN)

(73) Assignee: SUVEN LIFE SCIENCES LIMITED, Hyderabad-Telangana (IN)

( * ) Notice: Subject to any disclaimer, the term of this patent is extended or adjusted under 35 U.S.C. 154(b) by 857 days.

(21) Appl. No.: 17/285,432

(22) PCT Filed: Oct. 16, 2019

(86) PCT No.: PCT/IB2019/058815
§ 371 (c)(1),
(2) Date: Apr. 14, 2021

(87) PCT Pub. No.: WO2020/079606
PCT Pub. Date: Apr. 23, 2020

(65) Prior Publication Data
US 2021/0340148 A1    Nov. 4, 2021

(30) Foreign Application Priority Data

Oct. 17, 2018 (IN) .............................. 201841039345

(51) Int. Cl.
| C07D 487/04 | (2006.01) |
| A61K 45/06 | (2006.01) |
| A61P 1/00 | (2006.01) |
| A61P 25/00 | (2006.01) |

(52) U.S. Cl.
CPC ............ *C07D 487/04* (2013.01); *A61K 45/06* (2013.01); *A61P 1/00* (2018.01); *A61P 25/00* (2018.01)

(58) Field of Classification Search
None
See application file for complete search history.

(56) References Cited

U.S. PATENT DOCUMENTS

2019/0343812 A1    11/2019  Nirogi et al.
2020/0237761 A1    7/2020   Nirogi et al.

FOREIGN PATENT DOCUMENTS

| WO | 2018042362 A1 | 3/2018 |
| WO | 2018063552 A1 | 4/2018 |
| WO | 2019077517 A1 | 4/2019 |

OTHER PUBLICATIONS

Douglas C. Beshore et al., MK-7622: a First in Class M1 Positive Allosteric Modulator Development Candidate, ACS Medicinal Chemistry Letters, Apr. 30, 2018, 201897652-656.
John B. Furness et al, Muscarinic Receptor 1 Allosteric Modulators Stimulate Colorectal Emptying in Dog, Mouse, and Rat, and Resolve Constipation, Neurogastroenterology & Motility, 2019;00:e13692.
Khan, et al., M1 is a Major Subtype of Muscarinic Acetylcholine Receptors on Mouse Colonic Epithelial Cells, J Gastroenterol, 2013; 48:885-896.
Emi Kurimoto et al., An Approach to Discovering Novel Muscarinic M1 Receptor Positive Allosteric Modulators with Potent Cognitive Improvement and Minimized Gastrointestinal Dysfunction, Journal of Pharmacol and Experimental Therapeutics, 2018; 364: 23-37.
Allan I. Levey, Immunological Localization of m1-m5 Muscarinic Acetylcholine Receptors in Peripheral Tissues and Brain, Life Sciences, 1993, vol. 52, 441-448.
Christopher J. Langmead et al, Muscarinic Acetylcholine Receptors as CNS Drug Targets, Pharmacology & Therapeutics 117 (2008), 232-243.
Allan I. Levey, Muscarinic Acetylcholine Receptor Expression in Memory Circuits: Implications for Treatment of Alzheimer Disease, Proc. Natl. Acad. Sci. USA, vol. 93, pp. 13541-13546, Nov. 1996.
Jason M. Uslaner, et al, The Muscarinic M1 Receptor Positive Allosteric Modulator PQCA Improves Cognitive Measures in Rat, Cynomolgus Macaque, and Rhesus Macaque, Psychopharmacology, 2013, 225(1), 21-30.
Julie L. Engers et al, VU6007477, a Novel M1 Pam Based on Pyrrolo, [2,3-b], pyridine Carboxamide Core Devoid of Cholinergic Adverse Events, ACS Medicinal Chemistry Letters, vol. 9, No. 9, Sep. 4, 2018.
Yuu Sako, Emi Kurimoto et al., TAK-071, a Novel M1 Positive Allosteric Modulator with Low Cooperativity, Improves Cognitive Function in Rodents with Few Cholinergic Side Effects, Neuropsychopharmacology. 2019; 44(5):950-960.
Jana K. Shirey, A Selective Allosteric Potentiator of the M1 Muscarinic Acetylcholine Receptor Increases Activity of Medial Prefrontal Cortical Neurons and Restores Impairments in Reversal Learning, The Journal of Neuroscience, 2009, 29, 14271-14286.
European Patent Office, International Search Report, PCT/IB2019/058815, Rijswijk, Netherlands, Dec. 10, 2019.
European Patent Office, Written Opinion of the International Searching Authority, PCT/IB2019/058815, Munich, Germany, Dec. 10, 2019.

*Primary Examiner* — Leslie A. Royds Draper
(74) *Attorney, Agent, or Firm* — IpHorgan Ltd.

(57) ABSTRACT

The present invention relates to compounds of formula (I), or their isotopic forms, stereoisomers, tautomers or pharmaceutically acceptable salt(s) thereof as muscarinic M1 receptor positive allosteric modulators (M1 PAMs). The present invention describes the preparation, pharmaceutical composition and the use of such compounds. (I)

12 Claims, 1 Drawing Sheet

Figure 1A:
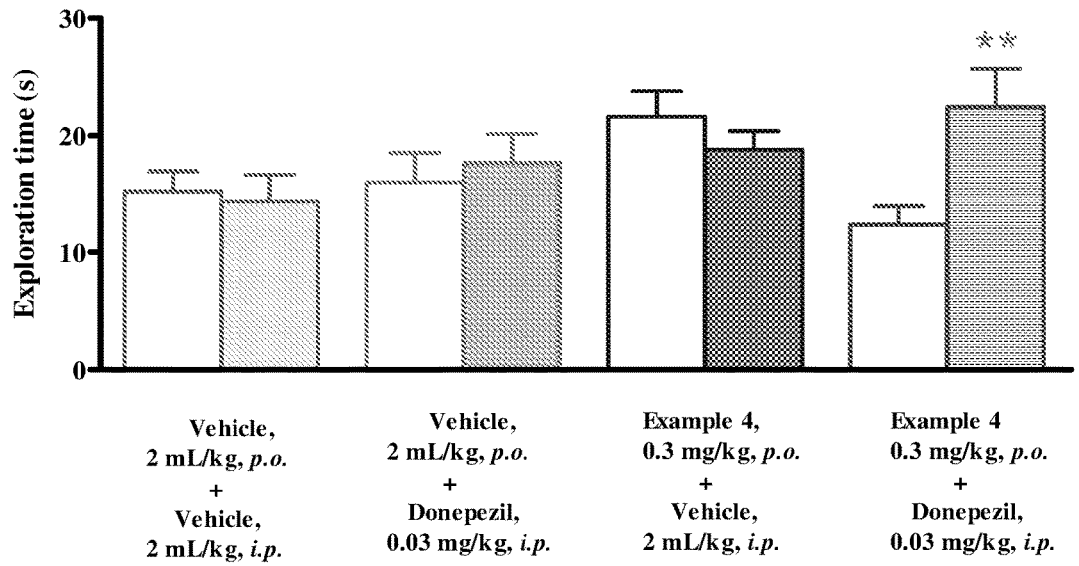

Data represents Mean ± SEM of Exploration Time (Student's paired two-tailed *t*-test), **$p<0.01$ vs. familiar object, n=10-11.

Data represents Mean ± SEM of Discriminative index (One-Way ANOVA followed by Bonferroni's *post hoc* test), ***$p<0.001$ vs. vehicle group, n=10-11.

PYRROLO-PYRIDAZINE DERIVATIVES AS MUSCARINIC M1 RECEPTOR POSITIVE ALLOSTERIC MODULATORS

CROSS REFERENCE TO RELATED APPLICATIONS

This application is a national stage completion application of PCT Application No. PCT/IB2019/058815, filed Oct. 16, 2019, and claims priority from India application No. 201841039345, filed Oct. 17, 2018. Each of these applications is incorporated by reference herein in its entirety.

FIELD OF INVENTION

The present invention relates to compounds of formula (I), or their isotopic forms, stereoisomers, tautomers or pharmaceutically acceptable salt(s) thereof as muscarinic M1 receptor positive allosteric modulators (M1 PAMs). The present invention describes the preparation, pharmaceutical composition and the use of such compounds.

BACKGROUND OF THE INVENTION

Muscarinic acetylcholine receptors (mAChRs) which belong to the class A family of G protein-coupled receptors (GPCRs), are widely expressed throughout the body. Five subtypes termed M1 through M5 that respond to the endogenous neurotransmitter acetylcholine (ACh) has been identified till date. They play key role in regulating the activity of many important functions of the central and peripheral nervous system including cognitive function. M1, M3 and M5 couple to Gq, whereas M2 and M4 couple via Gi/o to downstream signaling pathways and associated effector systems (*Critical Reviews in Neurobiology*, 1996, 10, 69-99; *Pharmacology & Therapeutics*, 2008, 117, 232-243). M2 and M3 are highly expressed in the periphery and are known to be involved in gastrointestinal (GI) motility and parasympathetic responses such as salivation (*Life Sciences*, 1993, 52, 441-448). The muscarinic M1 receptor is predominantly expressed in the brain regions such as cortex, hippocampus and amygdala which are involved in cognition, and therefore selective activation of the muscarinic M1 receptor would be expected to boost cognitive performance (*Proc. Natl. Acad. Sci. USA* 1996, 93, 13541-13546).

There is a high degree of conservation between muscarinic receptor subtypes at their orthosteric acetylcholine ligand binding sites which makes it difficult to identify a selective muscarinic M1 receptor agonist. To circumvent this issue, an alternative approach was adopted which consists of developing M1 PAMs that act at the less conserved allosteric binding site which exhibits less sequence homology. The M1 PAM, PQCA, (1-{[4-cyano-4-(pyridine-2-yl)piperidin-1-yl] methyl}-4-oxo-4H-quinolizine-3-carboxylic acid) is reported to be highly selective for muscarinic M1 receptor over the other muscarinic receptor subtypes and efficacious in several preclinical models of cognition (*Psychopharmacology*, 2013, 225(1), 21-30) with no gastrointestinal side effects at doses equal to or less than a fivefold margin from the minimum effective dose required to improve cognition. However, not all M1PAMs that cause cognitive enhancement show significant effects on the colon (Kurimoto E. et al., *J Pharmacol Exp Ther.* 2018; 364:23-37; Sako Y. & Kurimoto E. et al., *Neuropsychopharmacology.* 2019; 44(5):950-960. In preclinical studies, it was demonstrated that M1 activation increases neurotransmitter acetylcholine concentration in brain. Moreover, the M1 activation has potential as disease-modifying therapy for Alzheimer's disease (AD) by both shifting the β-amyloid precursor protein (βAPP) processing towards the non-amyloidogenic α-secretase pathway and by decreasing the tau hyper-phosphorylation. M1 PAMs have demonstrated to increase the generation of sAPPα in in-vitro system (*The Journal of Neuroscience*, 2009, 29, 14271-14286). Therefore, M1 PAMs provide an approach to target both symptomatic and disease-modifying treatment of cognitive disorders. Although M1PAMs have been shown to have utility in treating cognitive deficit disorders, there is also evidence that they enhance motility of content and fluid secretion in the colon of humans, dogs, rats, and mice. Thus, M1PAMs may have potential to facilitate physiological actions of acetylcholine (Ach) within enteric reflex pathways. M1 receptors are also prominent on the mucosal epithelium of the colon, where their activation increases fluid secretion (Khan M, Anisuzzaman A, Semba S, et al., *J Gastroenterol.* 2013; 48:885-896). Thus, M1PAMs could enhance colonic thrust and fluid secretion, both actions being of potential benefit in treating constipation. As the cholinergic muscarinic M1 receptor is expressed both in the brain and gastrointestinal nerve plexus, the compounds for treating gastric motility disorders ideally should have low to brain penetration, should show efficacy in peripheral system to be developed as a therapeutic drugs for treating constipation/motility disorders.

M1PAM compounds are in development both to enhance cognitive function with the specific aim of selectively treating Alzheimer's disease and for alleviation of gastrointestinal motility disorders. The M1 PAMs are shown to be safe for human use (Douglas C. Beshore et al., *ACS Med. Chem. Lett.* 201897652-656). PCT patent applications, WO2018042362, WO2015110370, WO2011084368, WO2011159554 and WO2011149801 have disclosed M1 PAM compounds with specific aim of treating AD. PCT patent application WO2018194181 and a publication (John B. Furness et al., *Neurogastroenterology & Motility.* 2019; 00:e13692) have been published with specific aim of treating gastro intestinal disorders. While several M1 PAMs have been disclosed in the literature till date, no drug acting as M1 PAM is launched in the market. Therefore, there remains an unmet need for developing novel and more effective M1 PAMs that modulate muscarinic M1 receptors to treat M1 mediated diseases such as Alzheimer's disease, gastrointestinal motility disorders and others as described herein.

SUMMARY OF THE INVENTION

In first aspect, the present invention relates to M1 PAMs of compound of formula (I),

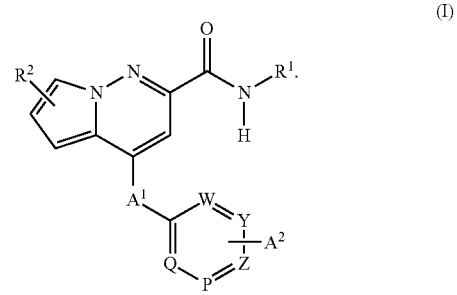

or an isotopic form, a stereoisomer, a tautomer or a pharmaceutically acceptable salt thereof.

Wherein:

$R^1$ is selected from —$(C_{1-6})$-alkyl, —$(C_{5-7})$-cycloalkyl, —$(C_{5-7})$-heterocycloalkyl, or —$(C_{6-10})$-aryl; each of which is optionally substituted with one or more groups selected from halogen, hydroxy, $NH_2$, $CH_2OH$ and $(C_{1-4})$-alkyl;

$R^2$ is selected from hydrogen, halogen, —$(C_{1-6})$-alkyl, —$(C_{3-6})$-cycloalkyl, or halo$(C_{1-4})$-alkyl;

$A^1$ is $CH_2$, CHF or $CF_2$;

P is independently selected from CH or N;

Q is independently selected from CH or N;

W is independently selected from CH or N;

Y is independently selected from CH or N;

Z is independently selected from CH or N;

$A^2$ is hydrogen, halogen, —$OR^2$, —$NHR^2$, —$NHCOR^2$, —CN, —$CONHR_2$, —$CON(R^2)_2$, —$(C_{1-4})$-alkyl, —$(C_{3-6})$-cycloalkyl, —$(C_{6-10})$-aryland-$(C_{5-10})$-heteroaryl; wherein each of the —$(C_{1-4})$-alkyl, —$(C_{3-6})$-cycloalkyl, —$(C_{6-10})$-aryland-$(C_{5-10})$-heteroaryl is optionally substituted with one or more substituents independently selected from halogen, —OR 2, —O—$(C_{1-4})$-alkyl, —S—$(C_{1-4})$-alkyl, —$N(CH_3)_2$, —$(C_{1-4})$-alkyl, —$(C_{3-6})$-cycloalkyl, halo$(C_{1-4})$-alkyl, —$NHR^2$, —$NHCOR^2$, —$CONHR^2$, —CN; wherein $R^2$ at each occurrence is independently selected from hydrogen, halogen, —$(C_{1-6})$-alkyl, —$(C_{3-6})$-cycloalkyl, or halo $(C_{1-4})$-alkyl;

or an isotopic form, a stereoisomer, a tautomer or a pharmaceutically acceptable salt thereof.

In another aspect, the present invention relates to the processes for preparing the compound of formula (I), or a stereoisomer or a pharmaceutically acceptable salt thereof.

In yet another aspect, the present invention relates to pharmaceutical composition containing a therapeutically effective amount of at least one compound of formula (I), or a stereoisomer or a pharmaceutically acceptable salt thereof and pharmaceutically acceptable excipients or carriers.

In yet another aspect, the present invention relates to a combination of compound of formula (I) or a stereoisomer or a pharmaceutically acceptable salt thereof, with other therapeutic agents selected from acetylcholinesterase inhibitors and NMDA receptor antagonist.

In yet another aspect, the present invention relates to compound of formula (I), or a stereoisomer or a pharmaceutically acceptable salt thereof, for use as muscarinic M1 receptor positive allosteric modulators.

In yet another aspect, the present invention relates to compound of formula (I), or a stereoisomer or a pharmaceutically acceptable salt thereof, for use in the treatment of disease or disorders selected from cognitive, mood, sleep disorders or gastrointestinal motility disorders.

In yet another aspect, the present invention relates to compound of formula (I), or a stereoisomer or a pharmaceutically acceptable salt thereof, for use in the treatment of diseases selected from Alzheimer's disease, schizophrenia or insomnia.

In another aspect, the present invention relates to a method for the treatment of disease or disorders related to muscarinic M1 receptor, comprising administering to a patient in need thereof, a therapeutically effective amount of a compound of formula (I), or a stereoisomer or a pharmaceutically acceptable salt thereof.

In yet another aspect, the present invention relates to use of the compound of formula (I), or a stereoisomer or a pharmaceutically acceptable salt thereof, for the manufacture of a medicament for the treatment of disease or disorders related to muscarinic M1 receptors.

In yet another aspect, the present invention relates to compound of formula (I) or a stereoisomer or a pharmaceutically acceptable salt thereof, for use in positive allosteric modulation of muscarinic M1 receptor.

BRIEF DESCRIPTION OF THE DIAGRAM

Figure 1B:
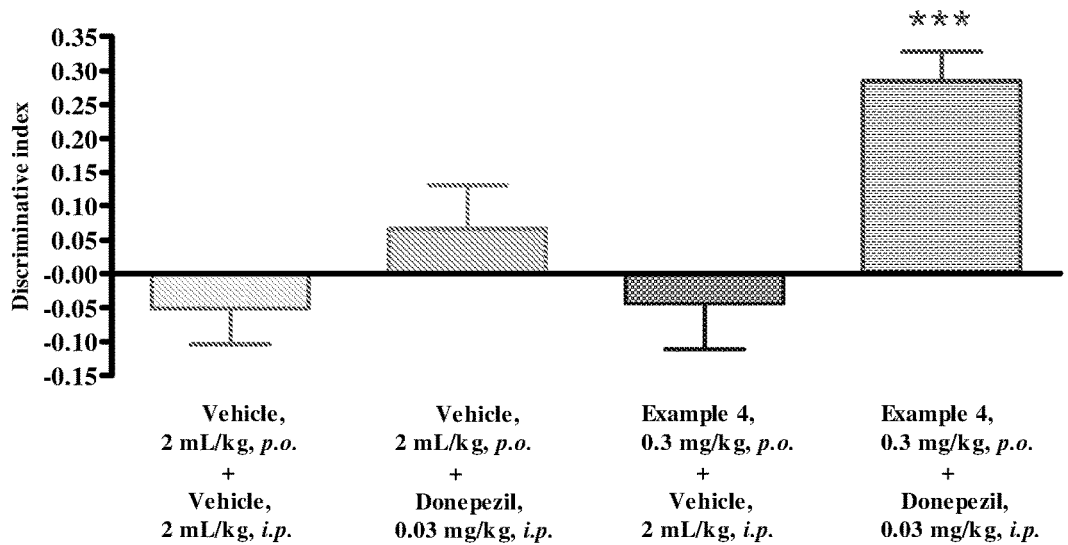

FIG. 1 depicts the results of the effect of a co-treatment of example 4 with donepezil on cognition enhancing properties using object recognition task model.

DETAILED DESCRIPTION OF THE INVENTION

Unless otherwise stated, the following terms used in the specification and claims have the meanings given below:

The term, "—$(C_{1-4})$-alkyl" as used herein refers to branched or straight chain aliphatic hydrocarbon containing 1 to 4 carbon atoms. Examples of $(C_{1-4})$-alkyl include methyl, ethyl, n-propyl, isopropyl, n-butyl, isobutyl, sec-butyl and tert-butyl. Preferably $(C_{1-4})$-alkyl is methyl, ethyl or isopropyl.

The term, "—$(C_{1-6})$-alkyl" as used herein refers to branched or straight chain aliphatic hydrocarbon containing 1 to 6 carbon atoms. Examples of $(C_{1-6})$-alkyl include methyl, ethyl, n-propyl, isopropyl, n-butyl, isobutyl, sec-butyl and tert-butyl. Preferably $(C_{1-6})$-alkyl is methyl, ethyl or isopropyl.

The term, "halogen" or "halo" as used herein refers to fluorine, chlorine, bromine or iodine. Preferably, halogen is fluorine, chlorine or bromine. More preferably halogen is fluorine or chlorine.

The term "halo$(C_{1-4})$-alkyl" as used herein refers to $(C_{1-4})$-alkyl as defined above wherein one or more hydrogen of the same or different carbon atom is substituted with same or different halogens. Examples of halo$(C_{1-4})$-alkyl include fluoromethyl, chloromethyl, fluoroethyl, difluoromethyl, dichloromethyl, trifluoromethyl, difluoroethyl and the like.

The term, "—$(C_{3-6})$-cycloalkyl" as used herein refers to saturated monocyclic hydrocarbon ring containing from three to six carbon atoms. Examples of $(C_{3-6})$-cycloalkyl group include cyclopropyl, cyclobutyl, cyclopentyl and cyclohexyl.

The term, "—$(C_{5-7})$-cycloalkyl" as used herein refers to saturated monocyclic hydrocarbon ring containing from five to seven carbon atoms. Examples of $(C_{5-7})$-cycloalkyl group include cyclopentyl, cyclohexyl, cycloheptyl and the like.

The term, "—$(C_{6-10})$-aryl" used herein refers to aromatic hydrocarbon rings containing six to ten carbon atoms. Examples of $(C_{6-10})$-aryl group include phenyl or naphthyl.

The term "—$(C_{5-7})$-heterocycloalkyl" used herein refers to saturated hydrocarbon rings containing one or two heteroatoms selected from oxygen, nitrogen and sulphur. Examples of $(C_{5-7})$-heterocycloalkyl group include tetrahydropyran, tetrahydrothiopyran, piperidine, azepane, morpholine, thiomorpholine, tetrahydrofuran, pyrrolidine or tetrahydrothiophene.

The term, "—$(C_{5-10})$-heteroaryl" as used herein refers to aromatic monocyclic or aromatic bicyclic heterocycle ring systems containing five to ten atoms. Examples of $(C_{5-10})$-heteroaryl group include 1,2,4-oxadiazolyl, 1,3,4-oxadiazolyl, 1,2,4-thiadiazolyl, 1,3,4-thiadiazolyl, triazolyl, tetrazolyl, triazinyl, furyl, imidazolyl, isoxazolyl, isothiazolyl, oxazolyl, pyrrolyl, pyrazolyl, thiazolyl, thienyl, pyridyl, pyrazinyl, pyrimidinyl, pyridazinyl, benzodioxolyl, benzofuranyl, benzofurazanyl, benzimidazolyl, benzopyrazolyl, benzothiazolyl, benzotriazolyl, benzothiophenyl, benzoxazepinyl, benzooxazinonyl, benzooxazolonyl, benzoxazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, isoquinolyl, quinolyl, phthalazinyl, naphthyridinyl, quinoxalinyl, quinazolinyl, and N-oxides thereof.

The phrase, "therapeutically effective amount" is defined as an amount of a compound of the present invention that (i) treats the particular disease, condition or disorder (ii) eliminates one or more symptoms of the particular disease, condition or disorder (iii) delays the onset of one or more symptoms of the particular disease, condition or disorder described herein.

The term, "isotopic form" as used herein refers to the compound of formula (I) wherein one or more atoms of compound of formula (I) are substituted by their respective isotopes. For example, isotopes of hydrogen include 2H (deuterium) and ³H (tritium).

The term, "stereoisomers" as used herein refers to isomers of compound of formula (I) that differ in the arrangement of their atoms in space. Compounds disclosed herein may exist as single stereoisomer, racemates and/or mixtures of enantiomers and/or diastereomers. All such single stereoisomer, racemates and mixtures thereof are intended to be within the scope of the present invention.

The term, "pharmaceutically acceptable salt" as used herein refers to salts of the active compound i.e. the compound of formula (I), and are prepared by reaction with the appropriate acid or acid derivative, depending on the particular substituents found on the compounds described herein.

The term, "cognitive disorder" as used herein refers to a group of mental health disorders that principally affect learning, memory, perception, and problem solving, and include amnesia, dementia, and delirium. Cognitive disorders can result due to disease, disorder, ailment or toxicity. Preferably the cognitive disorder is dementia. Example of dementia includes but not limited to, dementia in Alzheimer's disease, dementia in Parkinson's disease, dementia in Huntington's disease, dementia associated with Down syndrome, dementia associated with Tourette's syndrome, dementia associated with post menopause, frontotemporal dementia, Lewy body dementia, Vascular dementia, dementia in HIV, dementia in Creutzfeldt-Jakob disease, substance-induced persisting dementia, dementia in Pick's disease, dementia in schizophrenia and dementia in general medical conditions.

The term, "gastrointestinal motility disorder" as used herein refers to group of disorders that effects the gastrointestine tract include achalasia, non-achalasia esophageal motility disorders, dyspepsia, gastroparesis, chronic intestinal pseudo-obstruction, irritable bowel syndrome, and chronic constipation.

The term, "patient" as used herein refers to an animal. Preferably the term "patient" refers to mammal. The term mammal includes animals such as mice, rats, dogs, rabbits, pigs, monkeys, horses, pigeons, Xenopus laevis, zebrafish, guinea pigs and humans. More preferably the patient is human.

EMBODIMENTS

The present invention encompasses all the compounds described by the compound of formula (I) without any limitation, however, preferred aspects and elements of the invention are discussed herein in the form of the following embodiments.

In one embodiment, the present invention relates to the compound of formula (I), wherein: $R^1$ is selected from, —$(C_{1-6})$-alkyl, —$(C_{5-7})$-cycloalkyl, —$(C_{5-7})$-heterocycloalkyl, or —$(C_{6-10})$-aryl; each of which is optionally substituted with one or more groups selected from halogen, hydroxy, $NH_2$, $CH_2OH$ and $(C_{1-4})$-alkyl;

In one embodiment, the present invention relates to the compound of formula (I), wherein: $R^1$ is selected from the group consisting of;

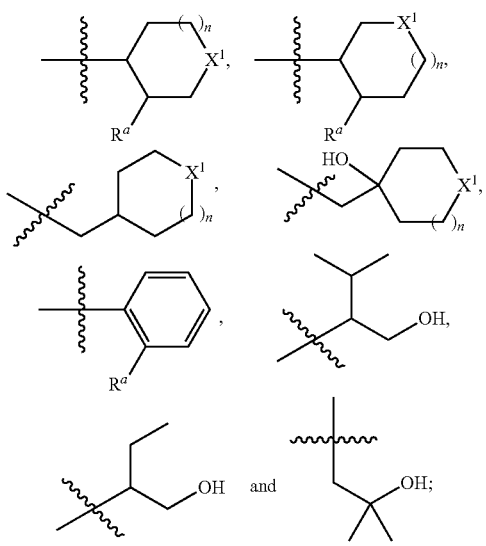

wherein
$R^a$ is independently selected from OH, F and $CH_2OH$;
$X^1$ is independently selected from $CH_2$, O and NH;
n is 0 or 1;
or an isotopic form, a stereoisomer or a pharmaceutically acceptable salt thereof.

In another embodiment, the present invention relates to the compound of formula (I), wherein:
$R^1$ is

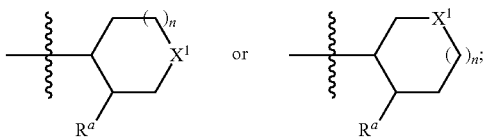

wherein $X^1$, $R^a$ and n are as defined above; or an isotopic form, a stereoisomer or a pharmaceutically acceptable salt thereof.

In another embodiment, the present invention relates to the compound of formula (I), wherein:
$R^1$ is

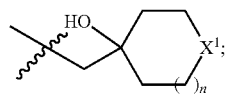

wherein $X^1$ and n are as defined above; or an isotopic form, a stereoisomer or a pharmaceutically acceptable salt thereof.

In another embodiment, the present invention relates to the compound of formula (I), wherein:
R1 is

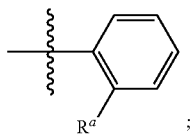

wherein $R^a$ is as defined above; or an isotopic form, a stereoisomer or a pharmaceutically acceptable salt thereof.

In another embodiment, the present invention relates to the compound of formula (I), wherein:
$R^1$ is

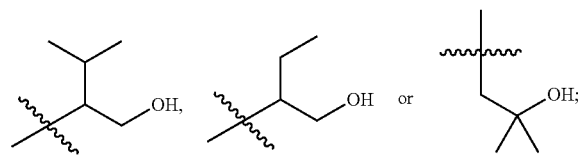

or an isotopic form, a stereoisomer or a pharmaceutically acceptable salt thereof.

In another embodiment, the present invention relates to the compound of formula (I), wherein: $A^2$ is selected from halogen, hydrogen, —O—$(C_{1-4})$-alkyl, —S—$(C_{1-4})$-alkyl, —N$(CH_3)_2$, —$(C_{1-4})$-alkyl, —$(C_{3-6})$-cycloalkyl, halo$(C_{1-4})$-alkyl, —OH, —$NH_2$, —$CONHR^2$, —$CON(R^2)_2$, or —CN; wherein $R^2$ at each occurrence is independently selected from hydrogen, halogen, —$(C_{1-6})$-alkyl, —$(C_{3-6})$-cycloalkyl, or halo$(C_{1-4})$-alkyl; or an isotopic form, a stereoisomer or a pharmaceutically acceptable salt thereof.

In another embodiment, the present invention relates to the compound of formula (I), wherein: ring $A^2$ is

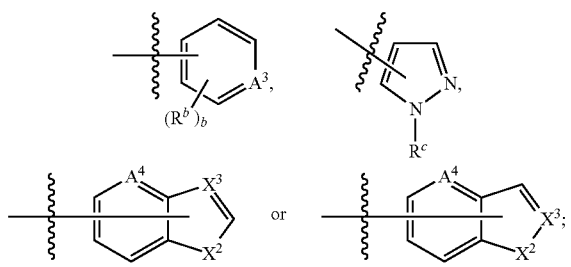

wherein $A^3$ is N or CH;
$A^4$ is CH or CF;
$R^b$ at each occurrence is independently selected from halogen, —O—$(C_{1-4})$-alkyl, —S—$(C_{1-4})$-alkyl, —N$(CH_3)_2$, —$(C_{1-4})$-alkyl, —$(C_{3-6})$-cycloalkyl, halo$(C_{1-4})$-alkyl, —OH, —$NH_2$, —$CONHR^2$, —CON$(R^2)_2$, —CN, phenyl, pyridyl, pyrazolyl, thiazolyl and oxazolyl; wherein phenyl, pyridyl, pyrazolyl, thiazolyl and oxazolyl are optionally substituted with one or more substituents selected from the group consisting of halogen, —$OR^2$, —$NHR^2$, —$NHCOR^2$, —$CONHR^2$, —CON$(R^2)_2$, —CN, —O—$(C_{1-2})$-alkyl, —S—$(C_{1-2})$-alkyl, —$(C_{1-2})$-alkyl and —$(C_{3-6})$-cycloalkyl; wherein $R^2$ at each occurrence is independently selected from hydrogen, halogen, —$(C_{1-6})$-alkyl, —$(C_{3-6})$-cycloalkyl, or halo$(C_{1-4})$-alkyl;
$R^c$ is hydrogen or —$(C_{1-4})$-alkyl;
$X^2$ is independently selected from NH, —N—$(C_{1-2})$-alkyl, O and S;
$X^3$ is independently selected from CH and N;
b is 0, 1 or 2;
"⁓⁓⁓" represents point of attachment;
or an isotopic form, a stereoisomer or a pharmaceutically acceptable salt thereof.

In another embodiment, the present invention relates to the compound of formula (I), wherein:
$A^2$ is

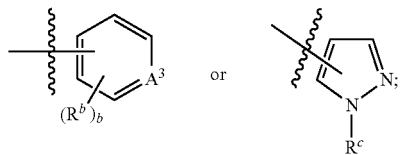

wherein $A^3$, $R^b$, and b are as defined in the first aspect; or an isotopic form, a stereoisomer or a pharmaceutically acceptable salt thereof.

In another embodiment, the present invention relates to the compound of formula (I), wherein:
$A^2$ is

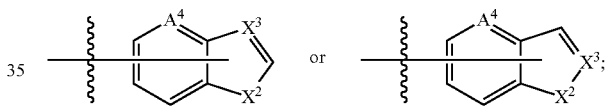

wherein $X^2$, $X^3$ and $A^4$ are as defined in the first aspect; or an isotopic form, a stereoisomer or a pharmaceutically acceptable salt thereof.

In another embodiment, the present invention relates to the compound of formula (I), wherein:
$A^2$ is

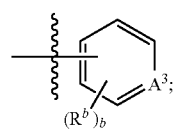

wherein $A^3$, $R^b$ and b are as defined in the first aspect; or an isotopic form, a stereoisomer or a pharmaceutically acceptable salt thereof.

In another embodiment, the present invention relates to the compound of formula (I), wherein: A is $CH_2$; or an isotopic form, a stereoisomer or a pharmaceutically acceptable salt thereof.

In another embodiment, the preferred compound of the invention is selected from the group consisting of:
N-[1-Hydroxy-cyclohexylmethyl]4-(4-chlorobenzyl)-pyrrolo[1,2-b]pyridazine-2-carboxamide;
N-[(1S,2S)-2-Hydroxycyclohexyl]-4-(4-chlorobenzyl)-pyrrolo[1,2-b]pyridazine-2-carboxamide;
N-[2-Hydroxy-2-methyl-propyl]-4-(4-chlorobenzyl)-pyrrolo[1,2-b]pyridazine-2-carboxamide;

N-[(1S,2S)-2-Hydroxycyclohexyl]-4-benzyl-pyrrolo[1,2-b]
pyridazine-2-carboxamide;
N-[(1S,2S)-2-Hydroxycyclohexyl]-4-(4-bromobenzyl)-pyrrolo[1,2-b]pyridazine-2-carboxamide;
N-[(4-Hydroxy-tetrahydro-pyran-4-ylmethyl)]-4-(4-chlorobenzyl)-pyrrolo[1,2-b]pyridazine-2-carboxamide;
N-[(1S,2S)-2-Hydroxycyclohexyl]-4-(3-fluorobenzyl)-pyrrolo[1,2-b]pyridazine-2-carboxamide;
N-[Cyclohexyl]-4-(4-chlorobenzyl)-pyrrolo[1,2-b]
pyridazine-2-carboxamide;
N-[Cyclopentyl]-4-(4-chlorobenzyl)-pyrrolo[1,2-b]
pyridazine-2-carboxamide;
N-[Cyclohexyl]-4-(4-bromobenzyl)-pyrrolo[1,2-b]
pyridazine-2-carboxamide;
N-[Cyclopentyl]-4-(4-bromobenzyl)-pyrrolo[1,2-b]
pyridazine-2-carboxamide;
N-[2-hydroxyethyl]-4-(4-bromobenzyl)-pyrrolo[1,2-b]
pyridazine-2-carboxamide;
N-[tetrahydrofuran-3-yl]-4-(3-fluorobenzyl)-pyrrolo[1,2-b]
pyridazine-2-carboxamide;
N-[Tetrahydropyran-4-yl]-4-(4-chlorobenzyl)-pyrrolo[1,2-b]pyridazine-2-carboxamide;
N-[2-hydroxyphenyl]-4-(4-bromobenzyl)-pyrrolo[1,2-b]
pyridazine-2-carboxamide;
N-[1-Hydroxymethyl-propyl]-4-(4-bromobenzyl)-pyrrolo[1,2-b]pyridazine-2-carboxamide;
N-[1-Hydroxymethyl-2-methylpropyl]-4-(4-bromobenzyl)-pyrrolo[1,2-b]pyridazine-2-carboxamide;
N-[Tetrahydrofuran-2-yl-methyl]-4-(4-bromobenzyl)-pyrrolo[1,2-b]pyridazine-2-carboxamide;
N-[2-hydroxy-2-methyl-propyl] 4-[4-(1-methyl-1H-pyrazol-4-yl)-benzyl]-pyrrolo[1,2-b]pyridazine-2-carboxamide;
N-[(1S,2S)-2-Hydroxy-cyclohexyl] 4-[4-(1-methyl-1H-pyrazol-4-yl)-benzyl]-pyrrolo[1,2-b]pyridazine-2-carboxamide;
N-[Tetrahydropyran-4-yl] 4-[4-(1-methyl-1H-pyrazol-4-yl)-benzyl]-pyrrolo[1,2-b]pyridazine-2-carboxamide;
N-[4-Hydroxy-tetrahydro-pyran-4-ylmethyl] 4-[4-(1-methyl-1H-pyrazol-4-yl)-benzyl]-pyrrolo[1,2-b]pyridazine-2-carboxamide;
N-[(1S,2S)-2-Hydroxycyclohexyl] 4-[4-(4-fluorophenyl)-benzyl]-pyrrolo[1,2-b]pyridazine-2-carboxamide;
N-[1-Hydroxy-cyclohexylmethyl] 4-[4-(1-methyl-1H-pyrazol-4-yl)-benzyl]-pyrrolo[1,2-b]pyridazine-2-carboxamide;
N-[(1S,2S)-2-Hydroxycyclohexyl] 4-[4-(2-methoxyphenyl)-benzyl]-pyrrolo[1,2-b]pyridazine-2-carboxamide;
N-[(1S,2S)-2-Hydroxycyclohexyl] 4-[4-(3-pyridyl)-benzyl]-pyrrolo[1,2-b]pyridazine-2-carboxamide;
N-[(1S,2S)-2-Hydroxycyclohexyl] 4-[4-(4-pyridyl)-benzyl]-pyrrolo[1,2-b]pyridazine-2-carboxamide;
N-[Tetrahydropyran-4-yl] 4-[4-(3-pyridyl)-benzyl]-pyrrolo[1,2-b]pyridazine-2-carboxamide;
N-[2-Hydroxy-2-methyl-propyl] 4-[4-(3-pyridyl)-benzyl]-pyrrolo[1,2-b]pyridazine-2-carboxamide;
N-[2-Hydroxy-2-methyl-propyl] 4-[4-(4-pyridyl)-benzyl]-pyrrolo[1,2-b]pyridazine-2-carboxamide;
N-[Tetrahydropyran-4-yl] 4-[4-(4-pyridyl)-benzyl]-pyrrolo[1,2-b]pyridazine-2-carboxamide;
N-[Tetrahydrofuran-3-yl] 4-[4-(1-methyl-1H-pyrazol-4-yl)-benzyl]-pyrrolo[1,2-b]pyridazine-2-carboxamide;
N-[Tetrahydrofuran-3-yl] 4-[4-(4-pyridyl)-benzyl]-pyrrolo[1,2-b]pyridazine-2-carboxamide;
N-[Tetrahydrofuran-3-yl] 4-[4-(3-pyridyl)-benzyl]-pyrrolo[1,2-b]pyridazine-2-carboxamide;
N-[Tetrahydrofuran-3-ylmethyl] 4-[4-(1-methyl-1H-pyrazol-4-yl)-benzyl]-pyrrolo[1,2-b]pyridazine-2-carboxamide;
N-[1-Hydroxymethyl-propyl] 4-[4-(1-methyl-1H-pyrazol-4-yl)-benzyl]-pyrrolo[1,2-b]pyridazine-2-carboxamide;
N-[1-Hydroxymethyl-2-methylpropyl] 4-[4-(1-methyl-1H-pyrazol-4-yl)-benzyl]-pyrrolo[1,2-b]pyridazine-2-carboxamide;
N-[3-Hydroxy-tetrahydropyran-4-yl] 4-[4-(1-methyl-1H-pyrazol-4-yl)-benzyl]-pyrrolo[1,2-b]pyridazine-2-carboxamide;
N-[(1S,2S)-2-Hydroxycyclohexyl]-4-[4-(2-chloropyridin-4-yl)-benzyl]-pyrrolo[1,2-b]pyridazine-2-carboxamide;
N-[(1S,2S)-2-Hydroxycyclohexyl]-4-[4-(5-cyanopyridin-3-yl)-benzyl]-pyrrolo[1,2-b]pyridazine-2-carboxamide;
N-[(1S,2S)-2-Hydroxycyclohexyl]-4-[4-(6-methylpyridin-2-yl)-benzyl]-pyrrolo[1,2-b]pyridazine-2-carboxamide;
N-[(1S,2S)-2-Hydroxycyclohexyl]-4-[4-(5-carbamoylpyridin-3-yl)-benzyl]-pyrrolo[1,2-b]pyridazine-2-carboxamide;
N-[(1S,2S)-2-Hydroxycyclohexyl]-4-[4-(6-fluoropyridin-2-yl)-benzyl]-pyrrolo[1,2-b]pyridazine-2-carboxamide;
N-[(1S,2S)-2-Hydroxycyclohexyl]-4-[4-(5-methylpyridin-3-yl)-benzyl]-pyrrolo[1,2-b]pyridazine-2-carboxamide;
N-[(1S,2S)-2-Hydroxycyclohexyl]-4-[4-(4-methoxypyridin-3-yl)-benzyl]-pyrrolo[1,2-b]pyridazine-2-carboxamide;
N-[(1S,2S)-2-Hydroxycyclohexyl]-4-[4-(3-methoxypyridin-4-yl)-benzyl]-pyrrolo[1,2-b]pyridazine-2-carboxamide;
N-[(1S,2S)-2-Hydroxycyclohexyl]-4-[4-(4-hydroxypyridin-3-yl)-benzyl]-pyrrolo[1,2-b]pyridazine-2-carboxamide;
N-[(1S,2S)-2-Hydroxycyclohexyl]-4-[4-(3-hydroxypyridin-4-yl)-benzyl]-pyrrolo[1,2-b]pyridazine-2-carboxamide;
N-[(1S,2S)-2-Hydroxycyclohexyl]-4-[4-(4-fluoropyridin-2-yl)-benzyl]-pyrrolo[1,2-b]pyridazine-2-carboxamide;
N-[(1S,2S)-2-Hydroxycyclohexyl]-4-[4-(2-fluoropyridin-4-yl-methyl)-benzyl]-pyrrolo[1,2-b]pyridazine-2-carboxamide;
N-[(1S,2S)-2-Hydroxycyclohexyl]-4-(4-cyanobenzyl)-pyrrolo[1,2-b]pyridazine-2-carboxamide;
N-[(1S,2S)-2-Hydroxycyclohexyl]-4-(4-carbamoylbenzyl)-pyrrolo[1,2-b]pyridazine-2-carboxamide;
N-[(1S,2S)-2-Hydroxycyclohexyl]-4-(4-methylcarbamoylbenzyl)-pyrrolo[1,2-b]pyridazine-2-carboxamide;
N-[(1S,2S)-2-Hydroxycyclohexyl]-4-(4-ethylcarbamoylbenzyl)-pyrrolo[1,2-b]pyridazine-2-carboxamide;
N-[(1S,2S)-2-Hydroxycyclohexyl]-4-(4-cyclopropylcarbamoylbenzyl)-pyrrolo[1,2-b]pyridazine-2-carboxamide;
N-[(1S,2S)-2-Hydroxycyclohexyl]-4-(4-isopropylcarbamoylbenzyl)-pyrrolo[1,2-b]pyridazine-2-carboxamide;
N-[(1S,2S)-2-Hydroxycyclohexyl]-4-(4-cyclopropylmethylcarbamoylbenzyl)-pyrrolo[1,2-b]pyridazine-2-carboxamide;
N-[(1S,2S)-2-Hydroxycyclohexyl]-4-(4-isobutylcarbamoylbenzyl)-pyrrolo[1,2-b]pyridazine-2-carboxamide;
N-[(1S,2S)-2-Hydroxycyclohexyl]-4-(3-methylcarbamoylbenzyl)-pyrrolo[1,2-b]pyridazine-2-carboxamide;
N-[(1S,2S)-2-Hydroxycyclohexyl]-4-(3-isobutylcarbamoylbenzyl)-pyrrolo[1,2-b]pyridazine-2-carboxamide;
N-[(1S,2S)-2-Hydroxycyclohexyl]-4-(2-isobutylcarbamoylbenzyl)-pyrrolo[1,2-b]pyridazine-2-carboxamide;
N-[(1S,2S)-2-Hydroxycyclohexyl]-4-[4-(4-cyanopyridin-2-yl)-benzyl]-pyrrolo[1,2-b]pyridazine-2-carboxamide;
N-[(1S,2S)-2-Hydroxycyclohexyl]-4-[4-(4-carbamoylpyridin-2-yl)-benzyl]-pyrrolo[1,2-b]pyridazine-2-carboxamide;

N-[(1S,2S)-2-Hydroxycyclohexyl]-4-[4-(4-methylcarbamoylpyridin-2-yl)-benzyl]-pyrrolo[1,2-b]pyridazine-2-carboxamide;

N-[(1S,2S)-2-Hydroxycyclohexyl]-4-[4-(2-cyclopropylcarbamoylpyridin-5-yl)-benzyl]-pyrrolo[1,2-b]pyridazine-2-carboxamide;

N-[(1S,2S)-2-Hydroxycyclohexyl]-4-[4-(5-cyclopropylcarbamoylpyridin-2-yl)-benzyl]-pyrrolo[1,2-b]pyridazine-2-carboxamide;

N-[(1S,2S)-2-Hydroxycyclohexyl]-4-[4-(3-cyclopropylcarbamoylpyridin-4-yl)-benzyl]-pyrrolo[1,2-b]pyridazine-2-carboxamide;

N-[(1S,2S)-2-Hydroxycyclohexyl]-4-[4-(4-methylcarbamoylphenyl)-benzyl]-pyrrolo[1,2-b]pyridazine-2-carboxamide;

N-[(1S,2S)-2-Hydroxycyclohexyl]-4-[4-(4-methylcarbamoylphenyl)-pyridin-3-yl-methyl]-pyrrolo[1,2-b]pyridazine-2-carboxamide;

N-[(1S,2S)-2-Hydroxycyclohexyl]-4-[4-(6-methylcarbamoylphenyl)-pyridin-3-yl-methyl]-pyrrolo[1,2-b]pyridazine-2-carboxamide and N-[(1S,2S)-2-Hydroxycyclohexyl]-4-[2-(4-methylcarbamoylphenyl)-pyridin-4-yl-methyl]-pyrrolo[1,2-b]pyridazine-2-carboxamide or a pharmaceutically acceptable salt thereof.

In another embodiment, the present invention relates to the process of preparation of compound of formula (I) as described herein.

Experimental Procedures

Scheme-1 depicts processes for the preparation of compound of formula (I), wherein:

Where in: X, R, $R^2$, $A^1$, $A^2$, P, Q, Y, W and Z are as defined as above.

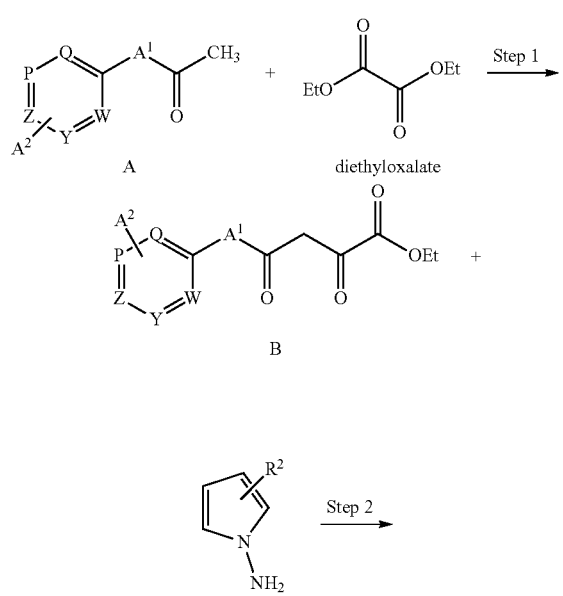

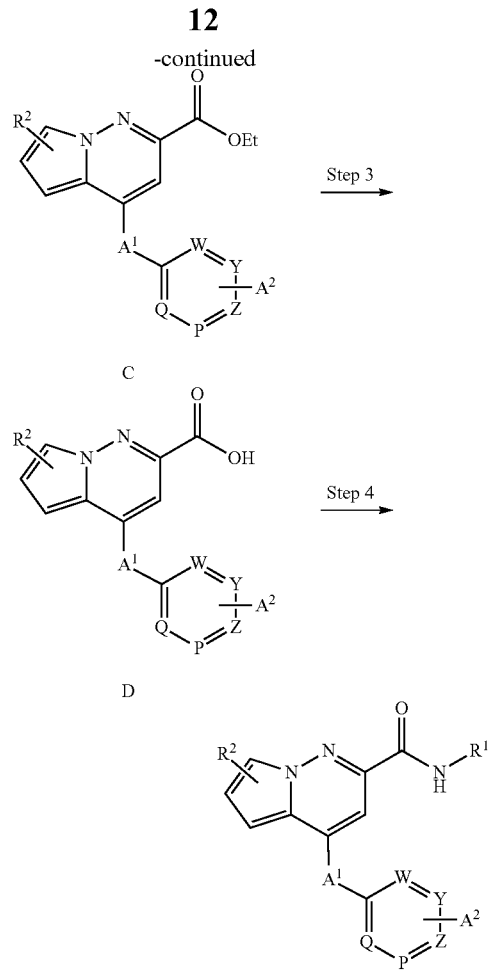

Compound of formula (I)

Step 1: Preparation of Compound of Formula B

The compound of formula A is reacted with diethyloxalate using sodium tert-butoxide, potassium tert-butoxide or cesium carbonate as base in toluene at 0° C. to room temperature (RT) for 10 to 16 hours to obtain the compound of formula B.

Step 2: Preparation of Compound of Formula C

The compound of formula B obtained in step 1 is reacted with substituted 1-aminopyrrole in presence of acid such as hydrochloric acid, hydrobromic acid or sulphuric acid, in a solvent selected from methanol, ethanol, isopropanol, THF or ethyleneglycol at the temperature range of 0 to 25° C. for 1 to 5 hours to obtain the compound of formula C.

Step 3: Preparation of Compound of Formula D

The compound of formula C obtained in step 2 is hydrolyzed using a base selected from Lithium hydroxide, sodium hydroxide or potassium hydroxide in a solvent selected from $H_2O$, THF, ethanol or methanol at the temperature range of 50 to 100° C. for 2 to 4 hours to obtain the compound of formula D.

Step 4: Preparation of Compound of Formula (I)

The compound of formula D obtained in step 3 is coupled with amine $R^1$—$NH_2$ in presence of coupling reagent, HATU, DCC or EDC and a base such as triethylamine, DIPEA, or DABCO in a solvent selected from DMF, THF, dichloromethane or 1,4-dioxane at RT for 6 to 16 hours to obtain the compound of formula (I).

Scheme 2: Alternate route for the preparation of compound of formula (I); Where in: X, R¹, R², A¹, A², P, Q, Y, W and Z are as defined as above.

selected from toluene, 1,4-dioxan, DMF or acetonitrile under reflux temperature for 2 to 12 hours to obtain the compound of formula H.

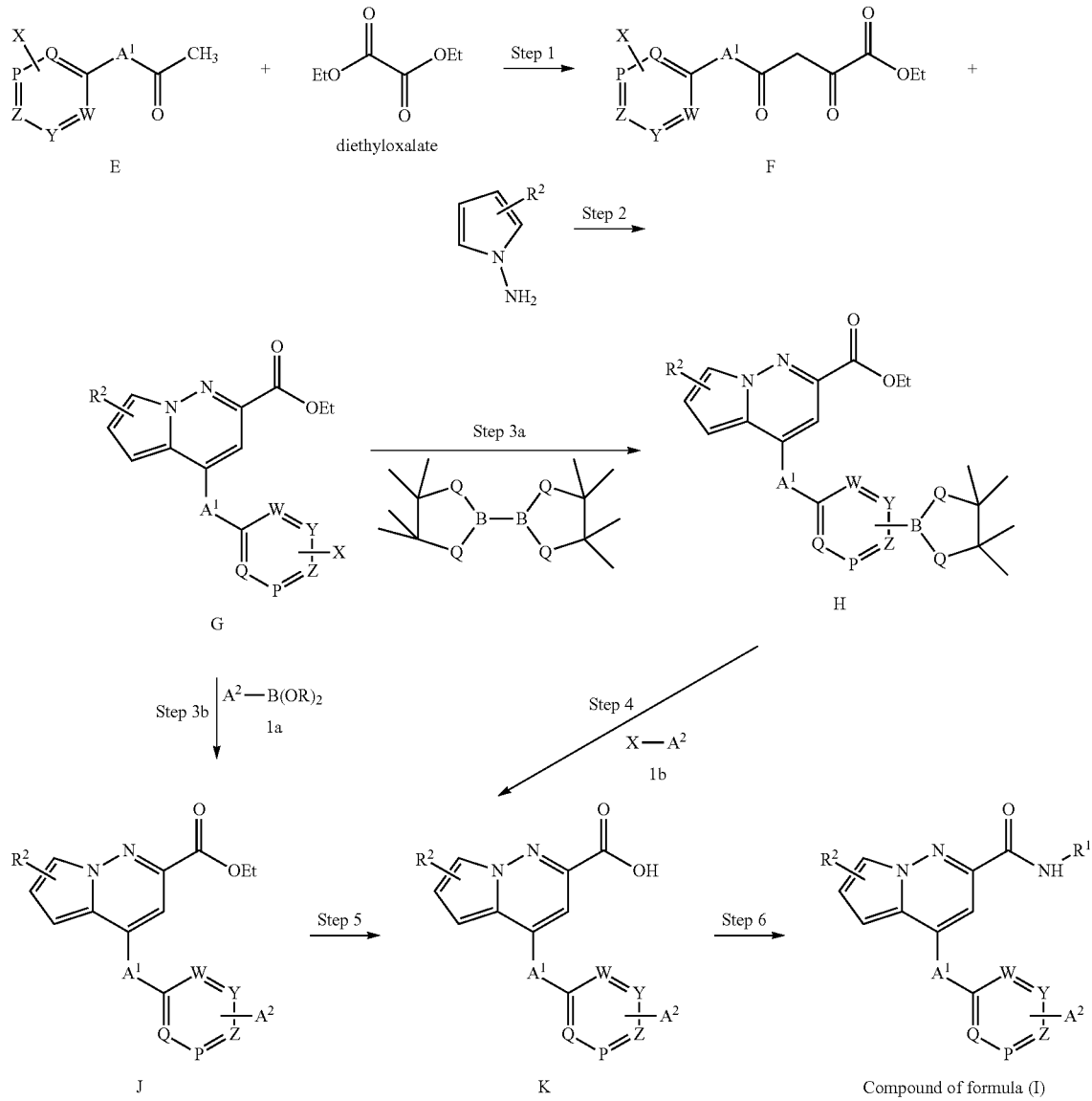

Step 1: Preparation of Compound of Formula F

The compound of formula E is reacted with diethyloxalate using sodium tert-butoxide, potassium tert-butoxide or cesium carbonate as base in toluene at 0° C. to room temperature (RT) for 10 to 16 hours to obtain the compound of formula F.

Step 2: Preparation of Compound of Formula G

The compound of formula F obtained in step 1 is reacted with substituted 1-aminopyrrolein presence of acid such as hydrochloric acid, hydrobromic acid or sulphuric acid, in a solvent selected from methanol, ethanol, isopropanol, THF or ethyleneglycol at the temperature range of 0 to 25° C. for 1 to 5 hours to obtain the compound of formula G.

Step 3a: Preparation of Compound of Formula H

The compound of formula G obtained in step 2 is reacted with bis(pinacolato)diboronin presence of potassium acetate, bis(tritert-butylphosphine)palladium in a solvent Step 3b: Preparation of Compound of Formula J The compound of formula G obtained in step 2 is reacted with aryl/hetroarylboronate ester or aryl/hetroaryl boronic acid of formula 1a and 1,1'-bis(diphenylphosphino)ferrocenepalladium(II)dichloride dichloromethane complex in presence of potassium acetate in a solvent selected from toluene or 1,4-dioxane at the temperature range of 90 to 110° C. for 7 to 9 hours to obtain the compound of formula J.

Step 4: Alternate Route for the Preparation of Compound of Formula J

The compound of formula H obtained in step 3a is reacted with compound A²-X of formula 1b (wherein X is Br, Cl) in presence of base such as cesium carbonate, potassium carbonate, or sodium carbonate; and [1,1'-bis(diphenylphosphino)ferrocene] di chloropalladium (II), 1:1 complex with dichloromethane in a mixture of solvents selected from THF, 1,4-dioxane, toluene and water in at the temperature range of 100 to 120° C. for 1 to 2 hours to obtain the compound of formula J.

Step 5: Preparation of Compound of Formula K

The compound of formula J obtained in step 3b or step 4 is hydrolyzed using a base selected from Lithium hydroxide, sodium hydroxide or potassium hydroxide in a solvent selected from $H_2O$, THF, ethanol or methanol at the temperature range of 50 to 100° C. for 2 to 4 hours to obtain the compound of formula K.

Step 6: Preparation of Compound of Formula (I)

The compound of formula K obtained in step 5 is coupled with amine $R^1$—$NH_2$ in presence of coupling reagent, HATU, DCC or EDC and a base such as triethylamine, DIPEA, or DABCO in a solvent selected from DMF, THF, dichloromethane or 1,4-dioxane at RT for 6 to 16 hours to obtain the compound of formula (I) (wherein A is $CH_2$).

Preparation of Compound of Formula (I) (Wherein $A^1$ is CHF or $CF_2$)

The compound of formula (I) (wherein $A^1$ is $CH_2$) is reacted with a brominating agent such as N-Bromosuccinimide (NBS) in the presence of a radical initiator such as azobisisobutyronitrile (AIBN) followed by hydrolysis under aqueous conditions to furnish an intermediate biarylmethanol/biarylketone derivative. The intermediate compound containing hydroxyl/oxo group is reacted with a fluorinating agent selected from HF-amine complex such as HF-pyridine, DAST or triethylamine trihydrofluoride and activating agent such as 1,1,2,2,3,3,4,4-nonafluorobutane-1-sulfonyl fluoride in the presence of triethylamine trihydrofluoride to obtain the compound of formula (I) (wherein A is CHF or $CF_2$).

Preparation of Pharmaceutically Acceptable Salt of Compound of Formula (I)

The compound of formula (I) can optionally be converted into its pharmaceutically acceptable salt by reaction with the appropriate acid or acid derivative. Suitable pharmaceutically acceptable salts will be apparent to those skilled in the art. The salts are formed with inorganic acids e.g., hydrochloric, hydrobromic, sulfuric, nitric & phosphoric acid or organic acids e.g., oxalic, succinic, maleic, acetic, fumaric, citric, malic, tartaric, benzoic, p-toluic, p-toluenesulfonic, benzenesulfonic acid, methanesulfonic or naphthalenesulfonic acid.

Preparation of Stereoisomers of Compound of Formula (I)

The stereoisomers of compounds of formula (I) may be prepared by one or more conventional ways presented below:

a. One or more of the reagents may be used in their optically active form.
b. Optically pure catalyst or chiral ligands along with metal catalyst may be employed in the reduction process. The metal catalyst may be rhodium, ruthenium, indium and the like. The chiral ligands may preferably be chiral phosphines.
c. The mixture of stereoisomers may be resolved by conventional methods such as forming diastereomeric salts with chiral acids or chiral amines or chiral amino alcohols, or chiral amino acids. The resulting mixture of diastereomers may then be separated by methods such as fractional crystallization, chromatography and the like, which is followed by an additional step of isolating the optically active product from the resolved material/salt.
d. The mixture of stereoisomers may be resolved by conventional methods such as microbial resolution, resolving the diastereomeric salts formed with chiral acids or chiral bases. Chiral acids that can be employed may be tartaric acid, mandelic acid, lactic acid, camphorsulfonic acid, amino acids and the like. Chiral bases that can be employed may be cinchona alkaloids, brucine or a basic amino acid such as lysine, arginine and the like.

In another embodiment, the suitable pharmaceutically acceptable salt includes hydrochloride, hydrobromide, oxalate, fumarate, tartrate, maleate and succinate.

In another aspect of the present invention, the compound of formula (I) are muscarinic M1 positive alloseteric modulators.

In another aspect, the present invention relates to a method of treatment of Alzheimer's disease comprising administering to a patient in need thereof, a therapeutically effective amount of compounds of formula (I) or a pharmaceutically acceptable salt thereof.

In another aspect, the present invention relates to a method of treatment of Alzheimer's diseases including mild Alzheimer's disease, moderate Alzheimer's disease, severe Alzheimer's disease, mild to moderate Alzheimer's disease or moderate to severe Alzheimer's disease, comprising administering to a patient in need thereof, a therapeutically effective amount of compounds of formula (I) or a pharmaceutically acceptable salt thereof.

In yet another aspect, the present invention relates to compound of formula (I) for use in the treatment of disease or disorder selected from cognitive disorder, pain, schizophrenia, sleep disorder or gastrointestinal motility disorders.

In yet another aspect, the present invention relates to use of the compound of formula (I) in the manufacture of medicament for the treatment of diseases or disorder selected from cognitive disorder, pain, schizophrenia, sleep disorder or gastrointestinal motility disorders.

In yet another aspect, the present invention relates to use of the compound of formula (I) in the manufacture of medicament for the treatment of diseases or disorder selected from cognitive disorder.

In yet another aspect, the present invention relates to use of the compound of formula (I) in the manufacture of medicament for the treatment of Alzheimer's disease.

In yet another embodiment, the present invention relates to the combination of compound of formula (I) with one or more other therapeutic agents acetylcholinesterase inhibitors and NMDA receptor antagonist.

In another embodiment, the compound of formula (I) of the present invention may be used in combination with one or more other therapeutic agents in the treatment of diseases or disorders for which the compound of formula (I) of the present invention have utility. Examples of the combinations of the compounds of present invention include combination with the therapeutic agents for the treatment of Alzheimer's disease, for example acetylcholinesterase inhibitors such as galantamine, rivastigmine, donepezil, and tacrine; and NMDA receptor antagonist such as memantine.

In yet another embodiment, the present invention relates to combination of compound of formula (I) with at least one therapeutic agents selected from galantamine, rivastigmine, donepezil, tacrine and memantine.

In yet another embodiment the present invention relates to the combination of compound of formula (I) with one or more other therapeutic agents acetylcholinesterase inhibitors and NMDA receptor antagonist for use in the treatment of cognitive disorder, pain, schizophrenia, sleep disorder and gastrointestinal motility disorders.

In yet another aspect, the present invention relates to the pharmaceutical composition of the compound of formula (I).

In order to use the compound of formula (I), or their stereoisomers and pharmaceutically acceptable salts thereof in therapy, they will normally be formulated into a pharmaceutical composition in accordance with standard pharmaceutical practice.

The pharmaceutical compositions of the present invention may be formulated in a conventional manner using one or more pharmaceutically acceptable excipients. The pharmaceutically acceptable excipients are diluents, disintegrants, binders, lubricants, glidants, polymers, coating agents, solvents, cosolvents, preservatives, wetting agents, thickening agents, antifoaming agents, sweetening agents, flavouring agents, antioxidants, colorants, solubilizers, plasticizer, dispersing agents and the like.

In yet another aspect, the active compounds of the invention may be formulated in the form of pills, tablets, coated tablets, capsules, powder, granules, pellets, patches, implants, films, liquids, semi-solids, gels, aerosols, emulsions, elixirs and the like. Such pharmaceutical compositions and processes for preparing same are well known in the art.

In yet another aspect, the pharmaceutical composition of the instant invention contains 1 to 90%, 5 to 75% and 10 to 60% by weight of the compounds of the instant invention or pharmaceutically acceptable salt thereof. The amount of the active compounds or its pharmaceutically acceptable salt in the pharmaceutical composition(s) can range from about 1 mg to about 500 mg or from about 5 mg to about 400 mg or from about 5 mg to about 250 mg or from about 7 mg to about 150 mg or in any range falling within the broader range of 1 mg to 500 mg.

The dose of the active compounds can vary depending on factors such as age and weight of patient, nature and severity of the disease to be treated and such other factors. Therefore, any reference regarding pharmacologically effective amount of the compounds of general formula (I), stereoisomers and pharmaceutically acceptable salts thereof refers to the aforementioned factors.

The following abbreviations are used herein:
AMP: Adenosine monophosphate
AUC: Area under the curve
CBr$_4$: Carbon tetrabromide
CCl$_4$: Carbon tetrachloride
C$_{max}$: Maximum concentration
CDCl$_3$: Deuterated chloroform
DAST: Diethylaminosulfur trifluoride
DABCO: 1,4-Diazabicyclo[2.2.2]octane
DCM: Dichloromethane
DCC: N,N'-Dicyclohexylcarbodiimide
DEA: Diethylamine
DIPEA: N,N-Diisopropylethylamine
DME: Dimethoxyethane
DMF: N,N-Dimethylformamide
DMSO: Dimethyl sulfoxide
EC$_{50}$: Half maximal effective concentration
EDC: Ethylene dichloride
HATU: 2-(7-Aza-1H-benzotriazole-1-yl)-1,1,3,3-tetramethyluronium hexafluorophosphate
HCl: Hydrochloric acid
H$_2$O: Water
h: hour(s)
IPA: Isopropyl alcohol
K$_2$CO$_3$: Potassium carbonate
LC-MS/MS: Liquid chromatography-Mass spectrometry/Mass spectrometry
MeOH: Methanol
MeOD: Deutrated methanol
NaBH$_4$: Sodium borohydride
NaOH: Sodium hydroxide
Na$_2$SO$_4$: Sodium sulphate
PBr$_3$: Phosphorus tribromide
PCl$_3$: Phosphorus trichloride
Pd(dppf)Cl$_2$·CH$_2$Cl$_2$: [1,1'-Bis(diphenylphosphino)ferrocene]dichloropalladium(II)
PPh$_3$: Triphenylphosphine
RT: Room temperature (25 to 30° C.)
ROA: Route of Administration
S.E.M.: Standard error of the mean
SOBr$_2$: Thionyl bromide
SOCl$_2$: Thionyl chloride
T: Temperature
THF: Tetrahydrofuran
T$_{1/2}$: Half-life time Example 1: N-[1-Hydroxy-cyclohexylmethyl]4-(4-chlorobenzyl)-pyrrolo[1,2-b]pyridazine-2-carboxamide

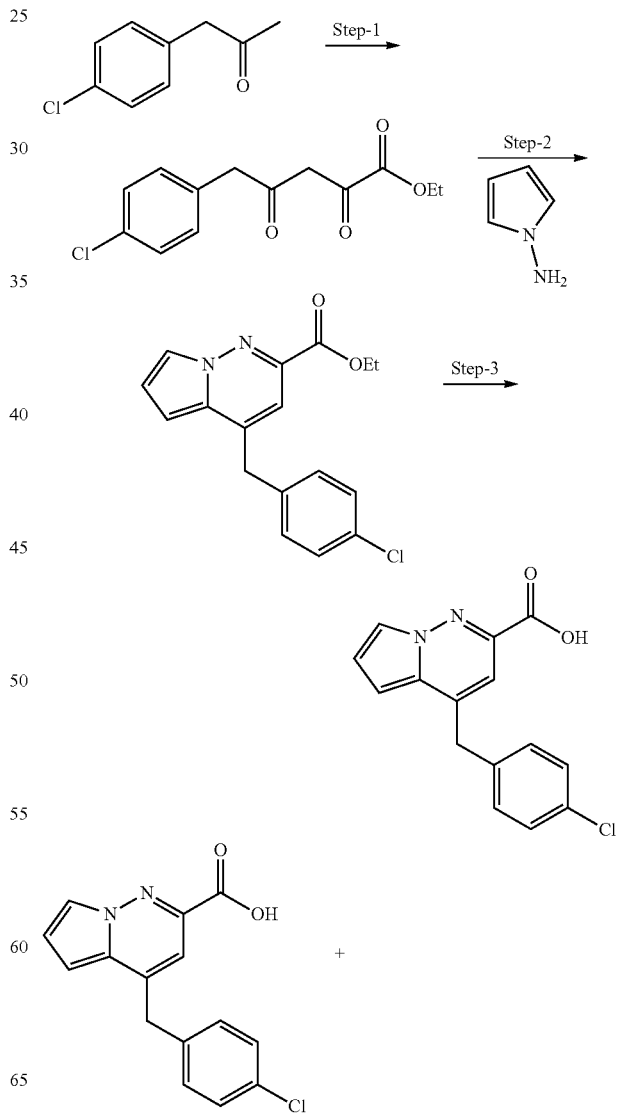

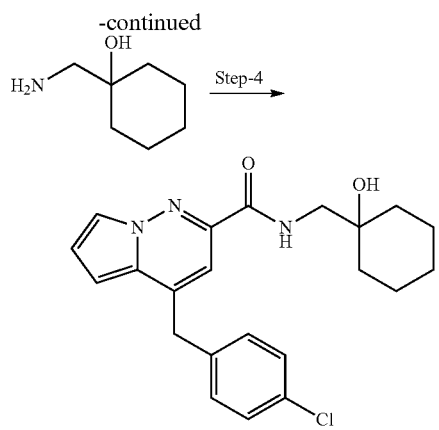

Step-1: To the stirred slurry of potassium tert-butoxide (4.31 g, 38.48 mmol) in dry toluene (60.0 mL) cooled at 0° C., a mixture of 1-(4-chlorophenyl)-2-propanone (5.0 g, 29.6 mmol) and diethyloxalate (4.82 mL, 35.52 mmol) was added over a period of 15 minutes. After stirring the reaction mixture at 0° C. for 2 h, the reaction temperature was raised to RT and was stirred for 16 h. The reaction mass was cooled to ice-bath temperature and was quenched by adding aqueous acetic acid until reaction pH reached 2.5. The reaction mass was diluted with EtOAc and the two layers were separated. The organic layer was washed with brine solution, dried over anhydrous $Na_2SO_4$ and the solvent was removed under reduced pressure to obtain step 1 product ethyl 5-(4-chlorophenyl)-2,4-dioxopentanoate (7.6 g) in 96% yield. $^1$H-NMR (400 MHz, CDCl$_3$): 1:1 Mixture of keto-enol forms δ 14.22 (bs, 0.5H), 7.38-7.25 (m, 2H), 7.20-7.10 (d, 2H), 6.34 (s, 0.5H), 4.40-4.30 (m, 2H), 3.74 (s, 1H), 3.67 (s, 1H), 2.16 (s, 1H), 1.42-1.32 (m, 3H); Mass (m/z); 269.1 271.2 (M+H)$^+$.

Step-2: To a solution of ethyl 5-(4-chlorophenyl)-2,4-dioxopentanoate (3.8 g, 14.17 mmol) as obtained in step-1, in ethanol cooled at 0° C., 1-aminopyrrole (1.22 g, 14.87 mmol) followed by 6N HCl (5.76 mL) was added. The reaction mass was maintained at this temperature for additional 1 h before diluting with water and DCM. The two layers were separated and the organic layer was washed with brine, dried over anhydrous $Na_2SO_4$ and the solvent was evaporated under reduced pressure to obtain a crude mass which was purified by silica gel column chromatography to obtain ethyl 4-(4-chlorobenzyl)-pyrrolo[1,2-b]pyridazine-2-carboxylate (2.5 g) in 56% yield. $^1$H-NMR (400 MHz, CDCl$_3$): δ 7.9 (s, 1H), 7.27 (d, 2H), 7.21 (d, 2H), 7.0 (s, 1H), 6.96 (dd, J=4.0 Hz, 3.2 Hz, 1H), 6.57 (d, J=8 Hz, 1H), 4.50 (q, 2H), 4.13 (s, 2H), 1.46 (t, 3H); Mass (m/z); 315.1, 317 (M+H)$^+$.

Step-3: To a stirred solution of ethyl 4-(4-chlorobenzyl)-pyrrolo[1,2-b]pyridazine-2-carboxylate as obtained in step-2 (2.5 g, 7.94 mmol) in a 1:1 mixture of ethanol and water (32.0 mL), sodium hydroxide (0.63 g, 15.88 mmol) was added. The temperature of the reaction mass was gradually raised and refluxed for 3 h. The reaction mass was cooled to RT, diluted with water (20.0 mL) and extracted with ether to remove the non acidic impurities. The aqueous layer thus obtained was cooled to ice-bath temperature and was acidified with 1N HCl to pH 5. The aqueous layer was extracted with chloroform which was dried over anhydrous $Na_2SO_4$ and the solvent was removed under reduced pressure to obtain 4-(4-chlorobenzyl)-pyrrolo[1,2-b]pyridazine-2-carboxylic acid (1.35 g) in 59% yield. $^1$H-NMR (400 MHz, CDCl$_3$): δ 7.84 (s, 1H), 7.30 (d, J=8.0 Hz, 2H), 7.20 (d, J=8.0 Hz, 2H), 7.07 (s, 1H), 7.02 (s, 1H), 6.65 (d, J=4.0 Hz, 1H), 4.15 (s, 2H); Mass (m/z); 287.1, 289.2 (M+H)$^+$.

Step-4: To a solution of 4-(4-chlorobenzyl)-pyrrolo[1,2-b]pyridazine-2-carboxylic acid (50.0 mg, 0.17 mmol) in DCM (1.7 mL) at 0-5° C. under N$_2$, was added TBTU (61.0 mg, 0.19 mmol) followed by addition of 1-aminomethylcyclohexanol (25 mg, 0.19 mmol) and DIPEA (0.06 mL, 0.35 mmol) and the reaction mass was stirred for 4 h. To the reaction mixture obtained ice water (5.0 mL) was added and extracted with DCM (10 mL×2). Organic layer was washed with brine solution (50 mL), dried over anhydrous $Na_2SO_4$ and the solvent was evaporated under reduced pressure to obtain the crude compound which was purified by flash chromatography using to afford the title compound N-[1-hydroxy-cyclohexylmethyl] 4-(4-chlorobenzyl)-pyrrolo[1,2-b]pyridazine-2-carboxamide (26.0 mg) in 38% yield. $^1$H-NMR (400 MHz, CDCl$_3$): δ 7.79 (s, 1H), 7.74 (bs, 1H), 7.27 (d, 2H), 7.21 (d, 2H), 7.15 (s, 1H), 6.93 (dd, J=4 Hz, 2.8 Hz 1H), 6.54 (d, J 3.6 Hz, 1H), 4.12 (s, 2H), 3.5 (d, 2H), 2.05 (bs, 1H), 1.65-1.45 (m, 10H); Mass (m/z); 398.2, 400.2 (M+H)$^+$.

Examples 2 to 18: The compounds of Example 2 to Example 18 were prepared by following the experimental procedures as described in the Example 1, with some non-critical variations.

| Example No. | Structure and IUPAC name | Characterization data |
|---|---|---|
| Example 2 | N-[(1S,2S)-2-Hydroxycyclohexyl]-4-(4-chlorobenzyl)-pyrrolo[1,2-b]pyridazine-2-carboxamide | $^1$H - NMR (400 MHz, CDCl$_3$): δ 7.74 (S, 1H), 7.44 (bs, 1H), 7.26-7.16 (m, 5H), 6.94 (t, J = 3.6 Hz, 1H), 6.54 (d, J = 3.6 Hz, 1H), 4.13 (S, 2H), 3.83-3.81 (m, 1H), 3.52-3.47 (m, 1H), 3.04 (bs, 1H), 2.13-2.08 (m, 2H), 1.8-1.7 (m, 1H), 1.57-1.31 (m, 4H); Mass (m/z); 384, 386 (M + H)$^+$. |

| Example No. | Structure and IUPAC name | Characterization data |
|---|---|---|
| Example 3 | 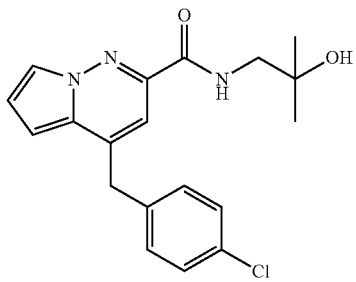<br>N-[2-Hydroxy-2-methyl-propyl]-4-(4-chlorobenzyl)-pyrrolo[1,2-b]pyridazine-2-carboxamide | $^1$H - NMR (400 MHz, CDCl$_3$): δ 7.84 (bs, 1H), 7.76 (s, 1H), 7.28 (d, 2H), 7.23 (d, 2H), 7.18 (s, 1H), 6.96 (dd, J = 4.0 Hz, 2.8 Hz, 1H), 6.57 (d, J = 4.4 Hz, 1H), 4.15 (s, 2H), 3.51 (d, 2H), 2.17 (bs, 1H), 1.32 (s, 6H); Mass (m/z); 358.2, 359.9 (M + H)$^+$. |
| Example 4 | 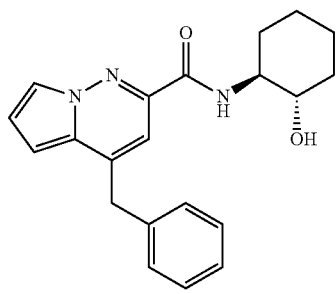<br>N-[(1S,2S)-2-Hydroxycyclohexyl]-4-benzyl-pyrrolo[1,2-b]pyridazine-2-carboxamide | $^1$H - NMR (400 MHz, CDCl$_3$): δ 7.73 (s, 1H), 7.44 (bs, 1H), 7.29-7.24 (m, 4H), 7.18 (s, 1H), 6.93 (dd, J = 4 Hz, 2.8 Hz, 1H), 6.59 (d, J = 4 Hz, 1H), 4.16 (s, 2H), 3.9-3.75 (m, 1H), 3.55-3.45 (m, 1H), 3.1 (bs, 1H), 2.14-2.06 (m, 2H), 1.79-1.76 (m, 2H), 1.42-1.33 (m, 4H); Mass (m/z); 350 (M + H)$^+$. |
| Example 5 | 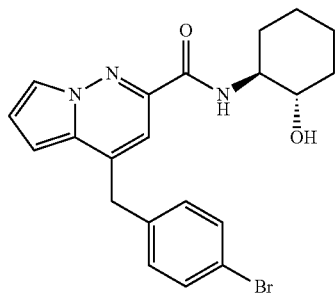<br>N-[(1S,2S)-2-Hydroxycyclohexyl]-4-(4-bromobenzyl)-pyrrolo[1,2-b]pyridazine-2-carboxamide | 1H - NMR (400 MHz, CDCl$_3$): δ 7.74 (s, 1H), 7.44 (bs, 1H), 7.42 (d, 2H), 7.16 (d, 2H), 7.13 (s, 1H), 6.94 (dd, J = 4 Hz, 3.2 Hz, 1H), 6.54 (d, J = 3.2 Hz, 1H), 4.11 (s, 2H), 3.85-3.75 (m, 1H), 3.55-3.45 (m, 1H), 3.05 (bs, 1H), 2.14-2.07 (m, 2H), 1.-1.77 (m, 2H), 1.42-1.30 (m, 4H); Mass (m/z); 428, 430 (M + H)$^+$. |

-continued

| Example No. | Structure and IUPAC name | Characterization data |
|---|---|---|
| Example 6 | 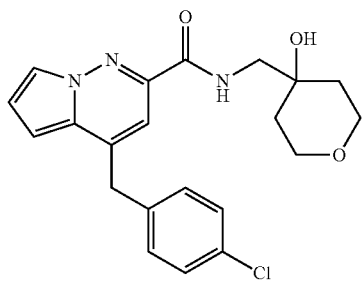<br>N-[(4-Hydroxy-tetrahydro-pyran-4-ylmethyl)]-4-(4-chlorobenzyl)-pyrrolo[1,2-b]pyridazine-2-carboxamide | $^{1}$H - NMR (400 MHz, CDCl$_{3}$): δ 7.85 (s, 1H), 7.75 (bs, 1H), 7.28 (d, 2H), 7.21 (d, 2H), 7.4 (s, 1H), 6.95 (dd, J = 4.4 Hz, 3.2 Hz, 1H), 6.56 (d, J = 4 Hz, 1H), 4.13 (s, 2H), 3.8-3.77 (m, 4H), 3.54 (d, 2H), 2.69 (bs, 1H), 1.74-1.7 (m, 2H), 1.62-1.53 (m, 2H); Mass (m/z); 398.1 (M − H)$^{+}$. |
| Example 7 | 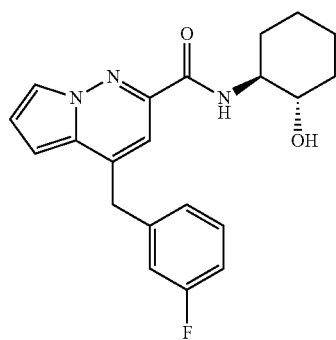<br>N-[(1S,2S)-2-Hydroxycyclohexyl]-4-(3-fluorobenzyl)-pyrrolo[1,2-b]pyridazine-2-carboxamide | $^{1}$H - NMR (400 MHz, CDCl$_{3}$): δ 7.75 (s, 1H), 7.45 (bs, 1H), 7.28-7.23 (m, 1H), 7.17 (s, 1H), 7.06 (dd, 1H), 6.96-6.91 (m, 3H), 6.56 (d, J = 4.4 Hz, 1H), 4.15 (s, 2H), 3.85-3.8 (m, 1H), 3.53-3.48 (m, 1H), 3.07 (bs, 1H), 2.14-2.07 (m, 2H), 1.8-1.77 (m, 2H), 1.46-1.28 (m, 4H); Mass (m/z); 368.2 (M + H)$^{+}$. |
| Example 8 | 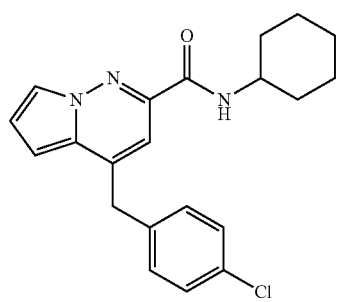<br>N-[(Cyclohexyl]-4-(4-chlorobenzyl)-pyrrolo[1,2-b]pyridazine-2-carboxamide | 1H - NMR (400 MHz, CDCl3): δ 7.73 (s, 1H), 7.28 (bs, 1H), 7.27-7.18 (m, 4H), 7.17 (s, 1H), 6.92 (dd, J = 4 Hz, 3.2 Hz, 1H), 6.52 (d, J = 3.6 Hz, 1H), 4.12 (s, 2H), 3.95-3.93 (m, 1H), 2.03-2.0 (m, 2H), 1.8-1.76 (m, 2H), 1.46-1.31 (m, 6H); Mass (m/z); 368.2, 370.1 (M + H)$^{+}$. |

| Example No. | Structure and IUPAC name | Characterization data |
|---|---|---|
| Example 9 | 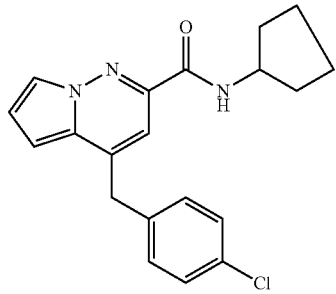<br>N-[Cyclopentyl]-4-(4-chlorobenzyl)-pyrrolo[1,2-b]pyridazine-2-carboxamide | $^1$H - NMR (400 MHz, CDCl$_3$): δ 7.73 (s, 1H), 7.37 (bs, 1H), 7.27 (d, J = 8.0 Hz, 2H), 7.2 (d, J = 8.0 Hz, 2H), 7.16 (s, 1H), 6.92 (dd, J = 4 Hz, 3.2 Hz, 1H), 6.53 (d, J = 4.4 Hz, 1H), 4.4 (m, 1H), 4.12 (s, 2H), 2.12-2.05 (m, 2H), 1.79-1.75 (m, 2H), 1.73-1.65 (m, 2H), 1.59-1.51 (m, 2H); Mass (m/z); 354.2, 356.1 (M + H)$^+$. |
| Example 10 | 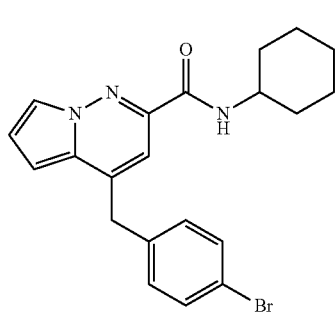<br>N-[Cyclohexyl]-4-(4-bromobenzyl)-pyrrolo[1,2-b]pyridazine-2-carboxamide | $^1$H - NMR (400 MHz, CDCl$_3$): δ 7.73 (s, 1H), 7.42 (d, 2H), 7.32 (bs, 1H), 7.17 (d, 2H), 7.13 (s, 1H), 6.92 (dd, J = 4.4 Hz, 3.2 Hz, 1H), 6.52 (d, J = 4 Hz, 1H), 4.10 (s, 2H), 4.0-3.9 (m, 1H), 2.03-2.0 (m, 2H), 1.8-1.75 (m, 2H), 1.46-1.28 (m, 6H); Mass (m/z); 412.1, 414.1 (M + H)$^+$. |
| Example 11 | 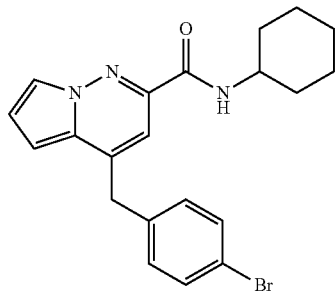<br>N-[Cyclopentyl]-4-(4-bromobenzyl)-pyrrolo[1,2-b]pyridazine-2-carboxamide | 1H - NMR (400 MHz, CDCl3): δ 7.73 (s, 1H), 7.42 (d, 2H), 7.36 (bs, 1H), 7.16 (d, 2H), 7.13 (s, 1H), 6.92 (dd, J = 3.6 Hz, 2.4 Hz, 1H), 6.52 (d, J = 4 Hz, 1H), 4.4-4.35 (m, 1H), 4.1 (s, 2H), 2.11-2.06 (m, 2H), 1.79-1.75 (m, 2H), 1.71-1.64 (m, 2H), 1.59-1.53 (m, 2H); Mass (m/z); 398, 400 (M + H)$^+$. |
| Example 12 | 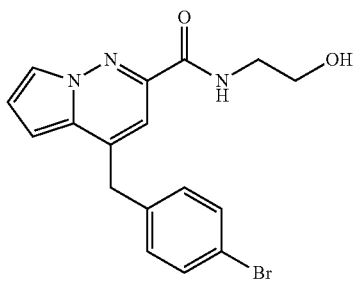<br>N-[2-hydroxyethyl]-4-(4-bromobenzyl)-pyrrolo[1,2-b]pyridazine-2-carboxamide | $^1$H - NMR (400 MHz, CDCl$_3$): δ 7.81 (bs, 1H), 7.73 (s, 1H), 7.43 (d, J = 8 Hz, 2H), 7.15 (d, J = 6.8 Hz, 3H), 6.94 (dd, J = 4 Hz, 3.2 Hz 1H), 6.55 (d, J = 4 Hz, 1H), 4.11 (s, 2H), 3.86 (d, 2H), 3.66-3.62 (m, 2H), 2.34 (bs, 1H); Mass (m/z); 374, 376 (M + H)$^+$. |

-continued

| Example No. | Structure and IUPAC name | Characterization data |
|---|---|---|
| Example 13 | 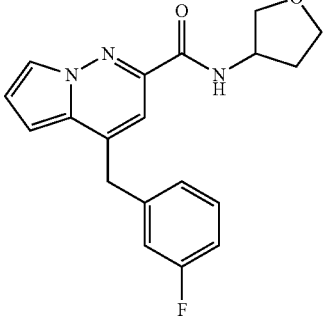<br>N-[tetrahydrofuran-3-yl]-4-(3-fluorobenzyl)-pyrrolo[1,2-b]pyridazine-2-carboxamide | $^1$H - NMR (400 MHz, CDCl$_3$): δ 7.74 (s, 1H), 7.6 (bs, 1H), 7.29-7.23 (m, 1H), 7.15 (s, 1H), 7.06 (d, J = 7.6 Hz 1H), 6.96-6.92 (m, 3H), 6.56 (d, J = 4 Hz, 1H), 4.71-4.7 (m, 1H), 4.15 (s, 2H), 4.05-4.01 (m, 1H), 3.96-3.92 (m, 1H), 3.89-3.8 (m, 2H), 2.39-2.34 (m, 1H), 1.99-1.95 (m, 1H); Mass (m/z); 340 (M + H)$^+$. |
| Example 14 | 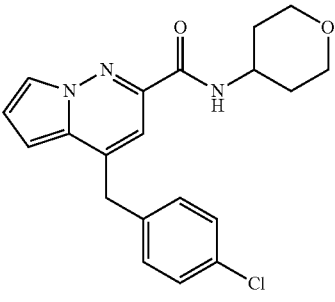<br>N-[Tetrahydropyran-4-yl]-4-(4-chlorobenzyl)-pyrrolo[1,2-b]pyridazine-2-carboxamide | 1H - NMR (400 MHz, CDCl$_3$): δ 7.75 (s, 1H), 7.38-7.32 (m, 1H), 7.28 (d, J = 8.4 Hz, 2H), 7.21 (d, J = 8.4 Hz, 2H), 7.15 (s, 1H), 6.94 (dd, J = 2.8, 4.0 Hz, 1H), 6.55 (dd, J = 1.2, 4.4 Hz, 1H), 4.23-4.13 (m, 1H), 4.13 (s, 2H), 4.06-3.98 (m, 2H), 3.58 (dt, J = 1.6, 11.6 Hz, 2H), 2.05-1.97 (m, 2H), 1.72-1.60 (m, 2H). 370.2, 372.2 (M + H)$^+$. |
| Example 15 | 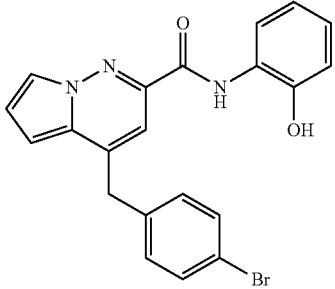<br>N-[2-hydroxyphenyl]-4-(4-bromobenzyl)-pyrrolo[1,2-b]pyridazine-2-carboxamide | $^1$H - NMR (400 MHz, CDCl$_3$): δ 9.5 (bs, 1H), 8.7 (s, 1H), 7.83 (s, 1H), 7.45 (d, J = 8.4 Hz, 2H), 7.25 (d, J = 3.6 Hz, 2H), 7.17 (d, 3H), 7.08 (d, J = 8 Hz 1H), 7.02-7.0 (m, 1H), 6.96 (t, J = 8 Hz, 1H), 6.62 (d, J = 4 Hz, 1H), 4.61 (s, 2H); Mass (m/z); 422, 424 (M + H)$^+$. |
| Example 16 | 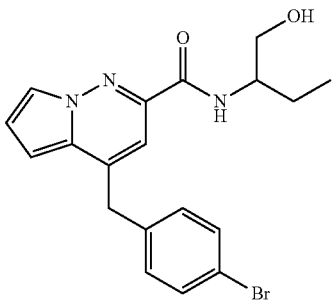<br>N-[1-Hydroxymethyl-propyl]-4-(4-bromobenzyl)-pyrrolo[1,2-b]pyridazine-2-carboxamide | $^1$H - NMR (400 MHz, CDCl$_3$): δ 7.74 (s, 1H), 7.55 (bs, 1H), 7.53 (d, J = 7.2 Hz, 2H), 7.15 (m, 3H), 6.94 (t, J = 3.6 Hz, 1H), 6.55 (d, J = 3.6 Hz, 1H), 4.11 (s, 2H), 4.09-4.03 (m, 1H), 3.84-3.8 (m, 1H), 3.74-3.7 (m, 1H), 2.36 (bs, 1H), 1.78-1.64 (m, 2H), 1.04 (t, J = 3H); Mass (m/z); 402, 404 (M + H)$^+$. |

| Example No. | Structure and IUPAC name | Characterization data |
|---|---|---|
| Example 17 | 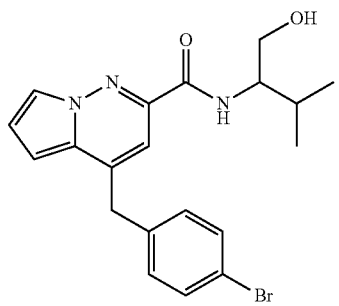<br>N-[1-Hydroxymethyl-2-methylpropyl]-4-(4-bromobenzyl)-pyrrolo[1,2-b]pyridazine-2-carboxamide | $^1$H - NMR (400 MHz, CDCl$_3$): δ 7.75 (s, 1H), 7.61 (d, J = 8.4 Hz, 1H), 7.43 (d, J = 8.0 Hz, 2H), 7.15 (s, 1H), 7.15 (d, J = 8.0 Hz, 2H), 6.94 (t, J = 3.6 Hz, 1H), 6.55 (d, J = 4.0 Hz, 1H), 4.13 (s, 2H), 3.98-3.90 (m, 1H), 3.88-3.75 (m, 2H), 2.34 (t, J = 5.2 Hz, 1H), 2.10-2.0 (m, 1H), 1.05 (t, J = 7.2 Hz, 6H). Mass (m/z); 416.1, 418.1 (M + H)$^+$. |
| Example 18 | 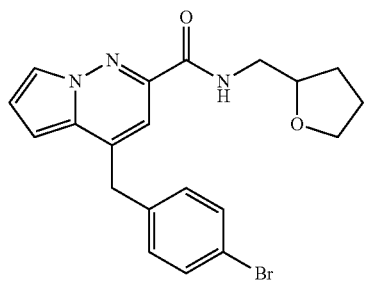<br>N-[Tetrahydrofuran-2-yl-methyl]-4-(4-bromobenzyl)-pyrrolo[1,2-b]pyridazine-2-carboxamide | $^1$H - NMR (400 MHz, CDCl$_3$): δ 7.74 (bs, 2H), 7.42 (d, J = 8.0 Hz, 2H), 7.15 (s, 1H), 7.15 (d, J = 8.0 Hz, 2H), 6.92 (t, J = 3.6 Hz, 1H), 6.53 (d, J = 4.0 Hz, 1H), 4.15-4.06 (m, 1H), 4.10 (s, 2H), 3.98-3.90 (m, 1H), 3.85-3.77 (m, 1H), 3.77-3.70 (m, 1H), 3.46-3.36 (m, 1H), 2.08-2.0 (m, 1H), 1.97-1.87 (m, 2H), 1.68-1.56 (m, 1H). Mass (m/z); 414.2, 416.0 (M + H)$^+$. |

Example 19: N-[2-hydroxy-2-methyl-propyl] 4-[4-(1-methyl-1H-pyrazol-4-yl)-benzyl]-pyrrolo[1,2-b]pyridazine-2-carboxamide

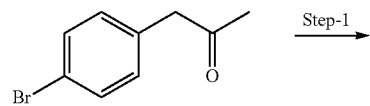 Step-1

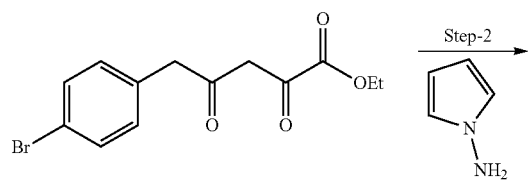 Step-2

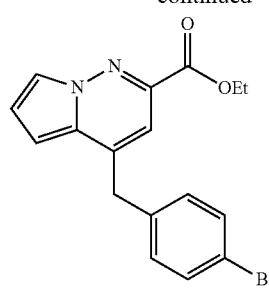 Step-3

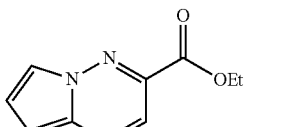

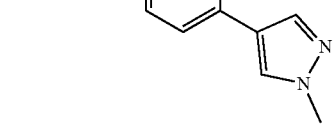 Step-4

-continued

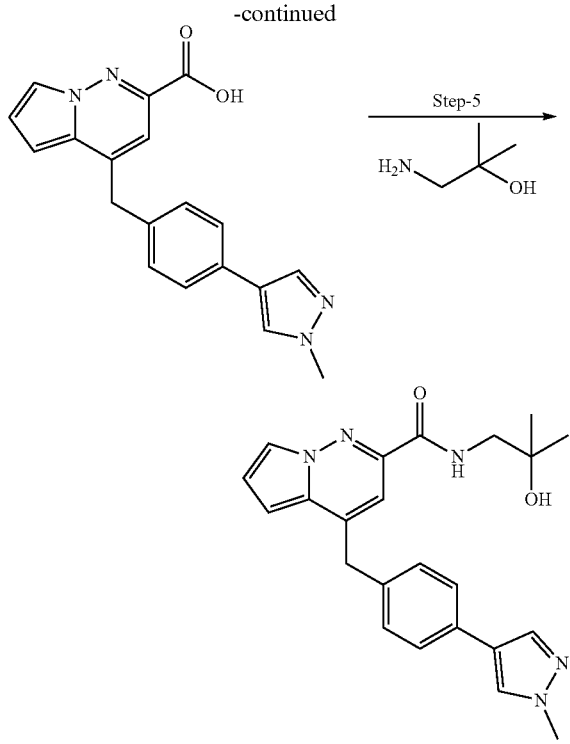

Step-1: To the stirred slurry of potassium tert-butoxide (6.84 g, 61.01 mmol) in dry toluene (93.0 mL) cooled at 0° C., a mixture of 1-(4-bromoophenyl)-2-propanone (10.0 g, 46.93 mmol). Diethyloxalate (7.64 mL, 56.31 mmol) in toulene (93.0 mL) was added over a period of 15 minutes. After stirring the reaction mixture at 0° C. for 2 h, the reaction temperature was raised to RT and was stirred at this temperature for 16 h. The reaction mass was cooled to ice-bath temperature and a solution of acetic acid (5.63 mL) and water (46.9 mL) were added until reaction pH reached to 5. The reaction mass was diluted with EtOAc and the two layers were separated. The organic layer was washed with brine solution, dried over anhydrous $Na_2SO_4$ and the solvent was removed under reduced pressure to obtain step 1 product ethyl 5-(4-bromophenyl)-2,4-dioxopentanoate (13.0 g) in 89% yield. $^1$H-NMR (400 MHz, $CDCl_3$): ~1:1 mixture of keto-enol isomers, 814.2 (bs, 0.5H), 7.48-7.44 (m, 2H), 7.12-7.06 (m, 2H), 6.34 (s, 0.5H), 4.36-4.30 (m, 2H), 3.72 (s, 1H), 3.66 (s, 1H), 2.16 (s, 1H), 1.39 (t, 3H); Mass (m/z); 312.9, 314.9 $(M+H)^+$.

Step-2: To a solution of ethyl 5-(4-bromophenyl)-2,4-dioxopentanoate (3.8 g, 14.17 mmol) as obtained in step-1, in ethanol cooled at 0° C., 1-aminopyrrole (1.22 g, 14.87 mmol) followed by 6N HCl (5.76 mL) was added. The reaction mass was maintained at this temperature for additional 1 h before diluting with water and DCM. The two layers were separated and the organic layer was washed with brine, dried over anhydrous $Na_2SO_4$ and the solvent was evaporated under reduced pressure to obtain a crude mass which was purified by silica gel column chromatography to obtain ethyl 4-(4-bromobenzyl)-pyrrolo[1,2-b]pyridazine-2-carboxylate (2.5 g) in 56% yield. $^1$H-NMR (400 MHz, $CDCl_3$): δ 7.91 (s, 1H), 7.48 (d, 2H), 7.15 (d, 2H), 7.0 (s, 1H), 6.96 (dd, J=4.2 Hz, 2.8 Hz, 1H), 6.56 (t, 1H), 4.51 (q, 2H), 4.11 (s, 2H), 1.45 (t, 3H); Mass (m/z); 359, 361 $(M+H)^+$.

Step-3: To a stirred solution of ethyl 4-(4-bromobenzyl)-pyrrolo[1,2-b]pyridazine-2-carboxylate as obtained in step-2 (1.28 g, 3.57 mmol) in a mixture of 1,4-dioxan (35.7 mL) and water (7.1 mL), potassium acetate (0.88 g, 8.92 mmol), N-methylpyrazoleboronic acid (0.58 g, 4.64 mmol) were added. The reaction mass was degassed for 15 minutes. The Bis(di-tert-butyl(4-dimethylaminophenyl)phosphine) dichloropalladium(II) $(Pd(amphos)_2Cl_2)$(0.25 g, 0.36 mmol) was added and the screw cap was tightened on the seal tube. The contents were heated to 100° C. for 5 h. The reaction mass was cooled to RT, diluted with EtOAc, washed with water followed by brine solution. The organic layer was dried over anhydrous $Na_2SO_4$ and the solvent was removed under reduced pressure to obtain a crude mass which was purified by silica gel column chromatography which afforded the title compound (ethyl 4-[4-(1-methyl-1H-pyrazol-4-yl)-benzyl]-pyrrolo[1,2-b]pyridazine-2-carboxylate) (0.91 g) in 71% yield. $^1$H-NMR (400 MHz, $CDCl_3$): δ 7.90 (s, 1H), 7.73 (s, 1H), 7.59 (s, 1H), 7.42 (d, J=8.0 Hz, 2H), 7.28 (d, J=8.0 Hz, 2H), 7.05 (s, 1H), 6.96 (dd, J=2.8, 4.0 Hz, 1H), 6.21 (d, J=4.0 Hz, 1H), 4.48 (q, 2H), 4.16 (s, 2H), 3.93 (s, 3H), 1.43 (t, J=6.8 Hz, 3H); Mass (m/z); 361.0 $(M+H)^+$.

Step-4: To a stirred solution of ethyl 4-[4-(1-methyl-1H-pyrazol-4-yl)-benzyl]-pyrrolo[1,2-b]pyridazine-2-carboxylate as obtained in step-3 (0.9 g, 2.52 mmol) in ethanol (5.0 mL) at r.t., sodium hydroxide (0.2 g, 5.1 mmol) dissolved in water (10.0 mL) was added. The reaction mixture was stirred at r.t. for 16 h. The reaction mass was diluted with water (10.0 mL) and extracted with ether to remove the non acidic impurities. The aqueous layer thus obtained was cooled to ice-bath temperature and was acidified with 1N HCl to pH 5. The aqueous layer was extracted with chloroform which was dried over anhydrous $Na_2SO_4$ and the solvent was removed under reduced pressure to obtain 4-[4-(1-methyl-1H-pyrazol-4-yl)-benzyl]-pyrrolo[1,2-b]pyridazine-2-carboxylic acid (0.63 g) in 75% yield. $^1$H-NMR (400 MHz, $CDCl_3$): δ 7.84 (s, 1H), 7.75 (s, 1H), 7.58 (s, 1H), 7.42 (d, J=8.0 Hz, 2H), 7.27 (d, J=8.0 Hz, 2H), 7.12 (s, 1H), 7.02 (dd, J=2.8, 4.0 Hz, 1H), 6.70 (d, J=4.0 Hz, 1H), 4.18 (s, 2H), 3.95 (s, 3H); Mass (m/z); 333.2 $(M+H)^+$.

Step-5: To a solution of 4-[4-(1-methyl-1H-pyrazol-4-yl)-benzyl]-pyrrolo[1,2-b]pyridazine-2-carboxylic acid (200.0 mg, 0.6 mmol) in DCM (10.0 mL) at 0 to 5° C. under $N_2$, DIPEA (0.21 mL, 1.2 mmol), TBTU (212.0 mg, 0.662 mmol) and 1-amino-2-methyl-2-propanol (54.0 mg, 0.6 mmol) were added sequentially. The reaction mass was gradually warmed to RT, and was stirred for 4 h. To the reaction mixture ice water (5.0 mL) was added and extracted with DCM (10 mL×2). Organic layer was washed with brine solution (50 mL), dried over anhydrous $Na_2SO_4$ and the solvent was evaporated under reduced pressure to obtain the crude compound which was purified by flash chromatography using to afford the title compound N-[2-hydroxy-2-methyl-propyl]4-[4-(1-methyl-1H-pyrazol-4-yl)-benzyl]-pyrrolo[1,2-b]pyridazine-2-carboxamide (153.0 mg) in 63% yield. $^1$H-NMR (400 MHz, $CDCl_3$): δ 7.83 (s, 1H), 7.74 (bs, 1H), 7.71 (s, 1H), 7.56 (s, 1H), 7.4 (d, 2H), 7.27 (d, 2H), 7.2 (s, 1H), 6.93 (s, 1H), 6.6 (d, J=3.2 Hz, 1H), 4.15 (s, 2H), 3.93 (s, 2H), 3.48 (d, 2H), 2.2 (bs, 1H), 1.3 (s, 6H); Mass (m/z); 404.2 $(M+H)^+$.

Examples 20 to 38: The compounds of Example 20 to Example 38 were prepared by following the experimental procedures as described in the Example 19, with some non-critical variations.

| Example No. | Structure and IUPAC name | Characterization data |
|---|---|---|
| Example 20 | 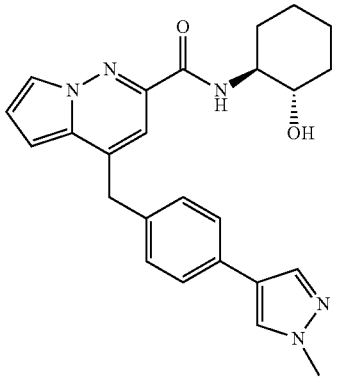<br>N-[(1S,2S)-2-Hydroxy-cyclohexyl] 4-[4-(1-methyl-1H-pyrazol-4-yl)-benzyl]-pyrrolo[1,2-b]pyridazine-2-carboxamide | $^1$H - NMR (400 MHz, CDCl$_3$): δ 7.73 (s, 1H), 7.71 (s, 1H), 7.56 (s, 1H), 7.44 (bs, 1H), 7.4 (d, 2H), 7.28-7.24 (d, 2H), 7.2 (s, 1H), 6.94 (t, J = 4 Hz, 1H), 6.6 (d, J = 4.4 Hz, 1H), 4.15 (s, 2H), 3.93 (s, 3H), 3.92-3.75 (m, 1H), 3.55-3.45 (m, 1H), 3.11 (bs, 1H), 2.06-2.02 (m, 2H), 1.78-1.76 (m, 2H), 1.41-1.35 (m, 4H); Mass (m/z); 430.3 (M + H)$^+$. |
| Example 21 | 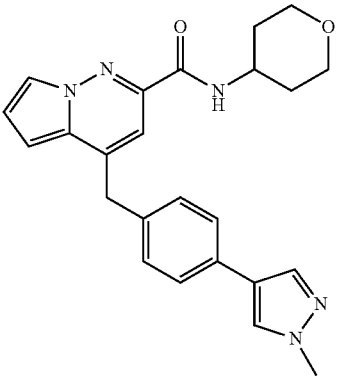<br>N-[Tetrahydropyran-4-yl] 4-[4-(1-methyl-1H-pyrazol-4-yl)-benzyl]-pyrrolo[1,2-b]pyridazine-2-carboxamide | $^1$H - NMR (400 MHz, CDCl$_3$): δ 7.74 (s, 1H), 7.71 (s, 1H), 7.56 (s, 1H), 7.4 (d, 2H), 7.36 (bs, 1H), 7.27 (d, 2H), 7.19 (s, 1H), 6.94 (dd, J = 4.4 Hz, 3.2 Hz, 1H), 6.6 (d, J = 4.4 Hz, 1H), 4.18-4.17 (m, 1H), 4.15 (s, 2H), 4.03-4.0 (m, 2H), 3.93 (s, 3H), 3.57-3.51 (m, 2H), 2.01-1.98 (m, 2H), 1.7-1.6 (m, 2H); Mass (m/z); 416 (M + H)$^+$. |
| Example 22 | 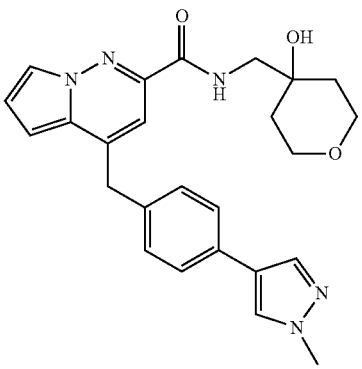<br>N-[4-Hydroxy-tetrahydro-pyran-4-ylmethyl] 4-[4-(1-methyl-1H-pyrazol-4-yl)-benzyl]-pyrrolo[1,2-b]pyridazine-2-carboxamide | $^1$H - NMR (400 MHz, CDCl$_3$): δ 7.83 (s, 1H), 7.73 (bs, 1H), 7.71 (s, 1H), 7.56 (s, 1H), 7.4 (d, 2H), 7.27 (d, 2H), 7.18 (s, 1H), 6.95 (dd, J = 4.4 Hz, 3.2 Hz, 1H), 6.62 (d, J = 4 Hz, 1H), 4.15 (s, 2H), 3.93 (s, 3H), 3.8-3.77 (m, 4H), 3.53 (d, 2H), 2.75 (bs, 1H), 1.77-1.7 (m, 2H), 1.62-1.55 (m, 2H); Mass (m/z); 446.3 (M + H)$^+$. |

| Example No. | Structure and IUPAC name | Characterization data |
|---|---|---|
| Example 23 | N-[(1S,2S)-2-Hydroxycyclohexyl] 4-[4-(4-fluorophenyl)-benzyl]-pyrrolo[1,2-b]pyridazine-2-carboxamide | $^1$H - NMR (400 MHz, CDCl$_3$): δ 7.74 (s, 1H), 7.52-7.45 (m, 5H), 7.34 (d, J = 8.0 Hz, 2H), 7.21 (s, 1H), 7.14-7.07 (m, 2H), 6.95 (dd, J = 4 Hz, 2.8 Hz, 1H), 6.62 (d, J = 4 Hz, 1H), 4.2 (s, 2H), 3.85-3.75 (m, 1H), 3.53-3.48 (m, 1H), 3.08 (bs, 1H), 2.14-2.07 (m, 2H), 1.80-1.77 (m, 2H), 1.45-1.33 (m, 4H); Mass (m/z); 444 (M + H)$^+$. |
| Example 24 | N-[1-Hydroxy-cyclohexylmethyl] 4-[4-(1-methyl-1H-pyrazol-4-yl)-benzyl]-pyrrolo[1,2-b]pyridazine-2-carboxamide | $^1$H - NMR (400 MHz, CDCl$_3$): δ 7.29 (s, 1H), 7.74 (bs, 1H), 7.71 (s, 1H), 7.56 (s, 1H), 7.4 (d, 2H), 7.27 (d, 2H), 7.2 (s, 1H), 6.93 (dd, J = 4 Hz, 2.8 Hz, 1H), 6.59 (d, J = 3.6 Hz, 1H), 4.15 (s, 2H), 3.93 (s, 3H), 3.5 (d, 2H), 2.07 (bs, 1H), 1.58-1.52 (m, 10H); Mass (m/z); 444.2 (M + H)$^+$. |
| Example 25 | N-[(1S,2S)-2-Hydroxycyclohexyl] 4-[4-(2-methoxyphenyl)-benzyl]-pyrrolo[1,2-b]pyridazine-2-carboxamide | $^1$H - NMR (400 MHz, CDCl$_3$): δ 7.74 (s, 1H), 7.46 (d, 2H), 7.43 (bs, 1H), 7.31-7.24 (m, 5H), 7.02-6.94 (m, 3H), 6.65 (d, J = 4 Hz, 1H), 4.19 (s, 2H), 3.9-3.8 (m, 1H), 3.79 (s, 3H), 3.52-3.48 (m, 1H), 3.09 (bs, 1H), 2.15-2.05 (m, 1H), 1.75-1.8 (m, 2H), 1.43-1.35 (m, 4H); Mass (m/z); 456.1 (M + H)$^+$. |

-continued

| Example No. | Structure and IUPAC name | Characterization data |
|---|---|---|
| Example 26 | 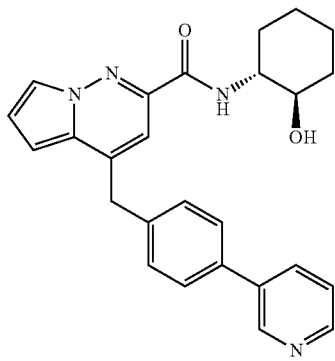<br>N-[(1S,2S)-2-Hydroxycyclohexyl] 4-[4-(3-pyridyl)-benzyl]-pyrrolo[1,2-b]pyridazine-2-carboxamide | $^1$H - NMR (400 MHz, CDCl$_3$): δ 8.02 (s, 1H), 8.58 (d, J = 4.4 Hz, 1H), 7.85 (d, J = 8 Hz, 1H), 7.75 (s, 1H), 7.52 (d, 2H), 7.45 (d, J = 7.6 Hz, 1H), 7.39-7.33 (m, 3H), 7.21 (s, 1H), 6.96 (dd, J = 4 Hz, 2.8 Hz, 1H), 6.62 (d, J = 3.6 Hz, 1H), 4.22 (s, 2H), 3.85-3.78 (m, 1H), 3.53-3.47 (m, 1H), 3.08 (bs, 1H), 2.1-2.08 (m, 2H), 1.8-1.77 (m, 2H), 1.42-1.38 (m, 4H); Mass (m/z); 427.1 (M + H)$^+$. |
| Example 27 | 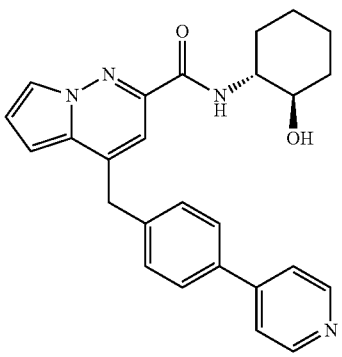<br>N-[(1S,2S)-2-Hydroxycyclohexyl] 4-[4-(4-pyridyl)-benzyl]-pyrrolo[1,2-b]pyridazine-2-carboxamide | $^1$H - NMR (400 MHz, CDCl$_3$): δ 8.64 (m, 2H), 7.76 (s, 1H), 7.58 (d, J = 8.0 Hz, 2H), 7.48-7.43 (m, 3H), 7.4 (d, 2H), 7.21 (s, 1H), 6.96 (dd, J = 2.6, 4.0 Hz, 1H), 6.61 (d, J = 4.0 Hz, 1H), 4.22 (s, 2H), 3.85-3.8 (m, 1H), 3.55-3.46 (m, 1H), 3.05 (bs, 1H), 2.14-2.09 (m, 2H), 1.8-1.77 (m, 2H), 1.42-1.35 (m, 4H); Mass (m/z); 427 (M + H)$^+$. |
| Example 28 | 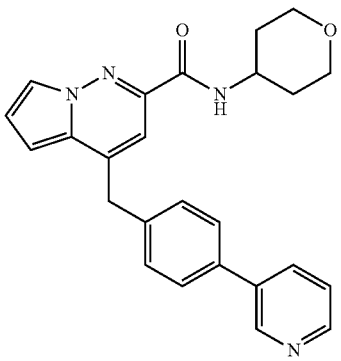<br>N-[Tetrahydropyran-4-yl] 4-[4-(3-pyridyl)-benzyl]-pyrrolo[1,2-b]pyridazine-2-carboxamide | $^1$H - NMR (400 MHz, CDCl$_3$): δ 8.82 (s, 1H), 8.58 (d, J = 3.6 Hz, 1H) 7.85 (d, J = 7.6 Hz, 1H), 7.76 (s, 1H), 7.53 (d, 2H), 7.4-7.33 (m, 4H), 7.21 (s, 1H), 6.96 (dd, J = 4 Hz, 2.4 Hz, 1H), 6.62 (d, J = 3.6 Hz, 1H), 4.22 (s, 2H), 4.19-4.16 (m, 1H), 4.05-3.95 (m, 2H), 3.57-3.52 (m, 2H), 2.01-1.98 (m, 2H), 1.7-1.63 (m, 2H); Mass (m/z); 413.1 (M + H)$^+$. |

| Example No. | Structure and IUPAC name | Characterization data |
|---|---|---|
| Example 29 | 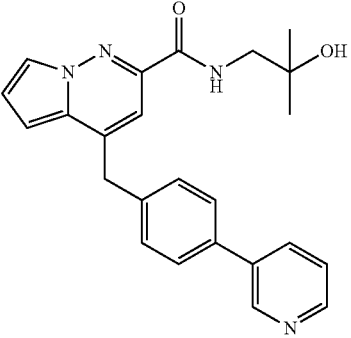<br>N-[2-Hydroxy-2-methyl-propyl] 4-[4-(3-pyridyl)-benzyl]-pyrrolo[1,2-b]pyridazine-2-carboxamide | $^1$H - NMR (400 MHz, CDCl$_3$): δ 8.82 (d, J = 1.6 Hz, 1H), 8.58 (d, J = 4.8 Hz, 1H), 7.85-7.83 (m, 2H), 7.76 (s, 1H), 7.53 (d, 2H), 7.4 (d, 2H), 7.36 (m, 1H), 7.2 (s, 1H), 6.96 (dd, J = 4 Hz, 3.2 Hz, 1H), 6.63 (d, J = 4 Hz, 1H), 4.22 (s, 2H), 3.49 (d, 2H), 2.19 (bs, 1H), 1.3 (s, 6H); Mass (m/z); 401.2 (M + H)$^+$. |
| Example 30 | 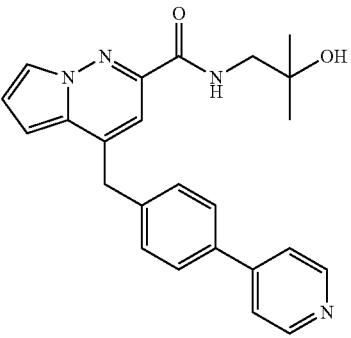<br>N-[2-Hydroxy-2-methyl-propyl] 4-[4-(4-pyridyl)-benzyl]-pyrrolo[1,2-b]pyridazine-2-carboxamide | $^1$H - NMR (400 MHz, CDCl$_3$): δ 8.64 (m, 2H), 7.84 (bs, 1H), 7.77 (s, 1H), 7.59 (d, 2H), 7.48 (m, 2H), 7.41 (d, 2H), 7.21 (s, 1H), 6.96 (dd, J = 4 Hz, 2.8 Hz, 1H), 6.62 (d, J = 4.4 Hz, 1H), 4.22 (s, 2H), 3.49 (d, 2H), 2.2 (bs, 1H), 1.3 (s, 6H); Mass (m/z); 401.2 (M + H)$^+$. |
| Example 31 | 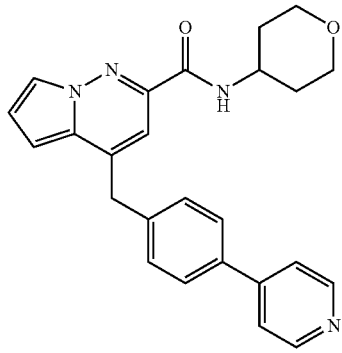<br>N-[Tetrahydropyran-4-yl] 4-[4-(4-pyridyl)-benzyl]-pyrrolo[1,2-b]pyridazine-2-carboxamide | $^1$H - NMR (400 MHz, CDCl$_3$): δ 8.64 (d, 2H), 7.76 (s, 1H), 7.58 (d, 2H), 7.48 (d, 2H), 7.41-7.35 (m, 3H), 7.2 (s, 1H), 6.9 (t, 1H), 6.61 (d, J = 3.6 Hz, 1H), 4.22 (s, 2H), 4.2-4.16 (m, 1H), 4.1-3.95 (m, 2H), 3.6-3.5 (m, 2H), 2.01-1.99 (m, 2H), 1.7-1.63 (m, 2H); Mass (m/z); 413.1 (M + H)$^+$. |

| Example No. | Structure and IUPAC name | Characterization data |
|---|---|---|
| Example 32 | 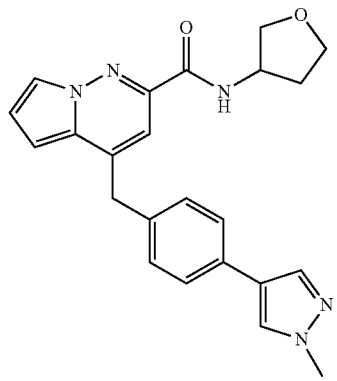<br>N-[Tetrahydrofuran-3-yl] 4-[4-(1-methyl-1H-pyrazol-4-yl)-benzyl]-pyrrolo[1,2-b]pyridazine-2-carboxamide | $^1$H - NMR (400 MHz, CDCl$_3$): δ 7.73 (s, 1H), 7.71 (s, 1H) 7.61 (bs, 1H), 7.56 (s, 1H), 7.4 (d, J = 8 Hz, 2H), 7.27 (d, 2H), 7.17 (s, 1H), 6.94 (t, J = 3.2 Hz, 1H), 6.6 (d, J = 3.6 Hz, 1H), 4.69 (m, 1H), 4.15 (s, 2H), 4.04-4.02 (m, 1H), 3.93 (s, 3H), 3.87-3.85 (m, 1H), 3.82-3.79 (m, 2H), 2.41-2.32 (m, 1H), 1.98-1.96 (m, 1H); Mass (m/z); 402.1 (M + H)$^+$. |
| Example 33 | 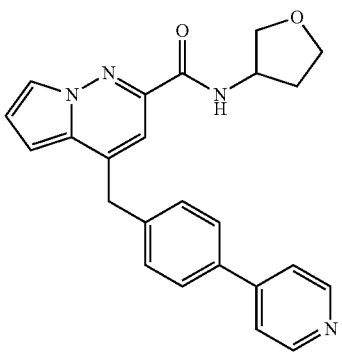<br>N-[Tetrahydrofuran-3-yl] 4-[4-(4-pyridyl)-benzyl]-pyrrolo[1,2-b]pyridazine-2-carboxamide | $^1$H - NMR (400 MHz, CDCl$_3$): δ 8.64 (d, J = 3.2 Hz 2H), 7.75 (s, 1H), 7.61 (bs, 1H), 7.58 (d, J = 8.0 Hz, 2H), 7.48 (d, J = 5.2 Hz, 2H), 7.4 (d, J = 8.0 Hz, 2H), 7.18 (s, 1H), 6.96 (t, J = 4 Hz, 1H), 6.62 (d, J = 4.0 Hz, 1H), 4.71-4.69 (m, 1H), 4.22 (s, 2H), 4.07-4.01 (m, 1H), 3.96-3.92 (m, 1H), 3.88-3.8 (m, 2H), 2.39-2.34 (m, 1H), 1.98-1.95 (m, 1H); Mass (m/z); 399.2 (M + H)$^+$. |
| Example 34 | 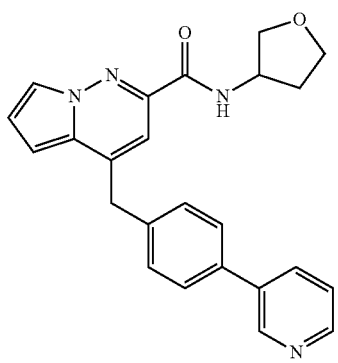<br>N-[Tetrahydrofuran-3-yl] 4-[4-(3-pyridyl)-benzyl]-pyrrolo[1,2-b]pyridazine-2-carboxamide | $^1$H - NMR (400 MHz, CDCl$_3$): δ 8.82 (s, 1H), 8.58 (d, J = 4 Hz 1H), 7.85 (d, J = 8 Hz, 1H), 7.75 (s, 1H), 7.61 (d, J = 7.6 Hz, 1H), 7.53 (d, J = 8 Hz, 2H), 7.39 (d, J = 8 Hz, 2H), 7.34 (bs, 1H), 7.19 (s, 1H), 6.96 (t, J = 3.6 Hz, 1H), 6.62 (d, J = 3.6 Hz, 1H), 4.71-4.7 (m, 1H), 4.21 (s, 2H), 4.07-4.01 (m, 1H), 3.96-3.92 (m, 1H), 3.88-3.8 (m, 2H), 2.41-2.32 (m, 1H), 2.01-1.93 (m, 1H); Mass (m/z); 399.2 (M + H)$^+$. |

| Example No. | Structure and IUPAC name | Characterization data |
|---|---|---|
| Example 35 | 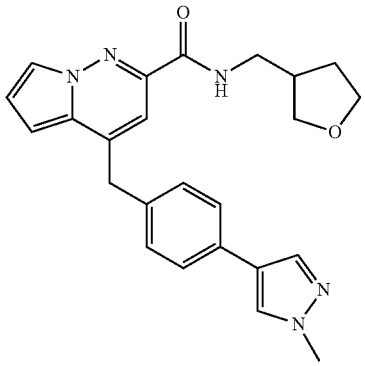<br>N-[Tetrahydrofuran-3-ylmethyl] 4-[4-(1-methyl-1H-pyrazol-4-yl)-benzyl]-pyrrolo[1,2-b]pyridazine-2-carboxamide | $^1$H - NMR (400 MHz, CDCl$_3$): δ7.80-7.70 (m, 3H), 7.56 (s, 1H), 7.39 (d, J = 8.4 Hz 2H), 7.19 (s, 1H), 6.91 (t, J = 3.2 Hz, 1H), 6.58 (d, J = 3.6 Hz, 1H), 4.15 (s, 2H), 4.15-4.06 (m, 1H), 3.93 (s, 3H), 3.85-3.78 (m, 1H), 3.77-3.70 (m, 1H), 3.46-3.38 (m, 1H), 2.06-2.0 (m, 1H), 1.97-1.89 (m, 2H). Mass (m/z); 416.1 (M + H)$^+$. |
| Example 36 | 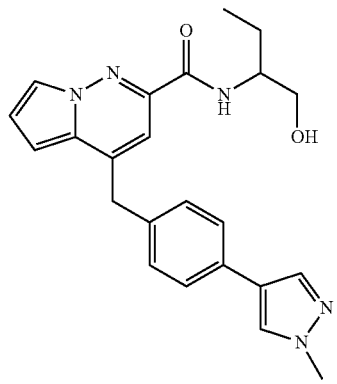<br>N-[1-Hydroxymethyl-propyl] 4-[4-(1-methyl-1H-pyrazol-4-yl)-benzyl]-pyrrolo[1,2-b]pyridazine-2-carboxamide | $^1$H - NMR (400 MHz, CDCl$_3$): δ7.74 (s, 1H), 7.71 (s, 1H), 7.56 (s, 1H), 7.56-7.51 (m, 1H), 7.40 (d, J = 8.4 Hz, 2H), 7.28 (d, J = 8.4 Hz, 2H), 7.19 (s, 1H), 6.94 (dd, J = 3.2, 4.0 Hz, 1H), 6.61 (d, J = 4.0 Hz, 1H), 4.15 (s, 2H), 4.08-4.02 (m, 1H), 3.93 (s, 3H), 3.86-3.78 (m, 1H), 3.76-3.68 (m, 1H), 2.45-2.38 (m, 1H), 1.80-1.60 (m, 2H), 1.02 (t, J = 7.2 Hz, 3H); Mass (m/z); 404.1 (M + H)$^+$. |
| Example 37 | 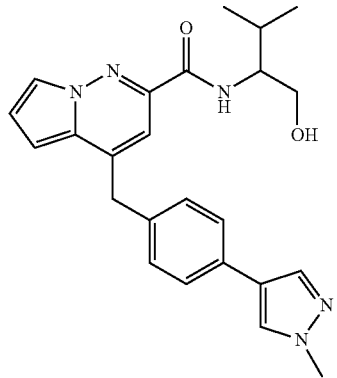<br>N-[1-Hydroxymethyl-2-methylpropyl] 4-[4-(1-methyl-1H-pyrazol-4-yl)-benzyl]-pyrrolo[1,2-b]pyridazine-2-carboxamide | $^1$H - NMR (400 MHz, CDCl$_3$): δ7.75 (s, 1H), 7.71 (s, 1H), 7.62 (d, J = 8.4 Hz, 1H), 7.54 (s, 1H), 7.40 (d, J = 8.0 Hz, 2H), 7.27 (d, J = 8.0 Hz, 2H), 7.20 (s, 1H), 6.94 (d, J = 3.6 Hz, 1H), 6.61 (d, J = 4.0 Hz, 1H), 4.15 (s, 2H), 3.93 (s, 3H), 3.92-3.88 (m, 1H), 3.87-3.75 (m, 2H), 2.36 (t, J = 5.2 Hz, 1H), 2.10-2.0 (m, 1H), 1.05 (t, J = 7.2 Hz, 6H); Mass (m/z); 418.2 (M + H)$^+$. |

| Example No. | Structure and IUPAC name | Characterization data |
|---|---|---|
| Example 38 | 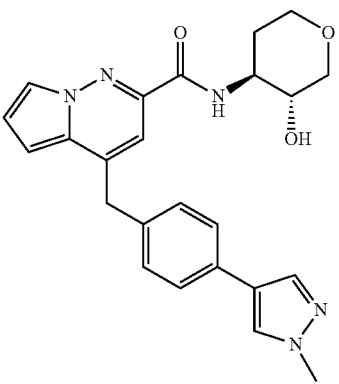<br>N-[3-Hydroxy-tetrahydropyran-4-yl] 4-[4-(1-methyl-1H-pyrazol-4-yl)-benzyl]-pyrrolo[1,2-b]pyridazine-2-carboxamide | $^1$H - NMR (400 MHz, CDCl$_3$): δ7.87 (d, J = 8.4 Hz, 1H), 7.76 (s, 1H), 7.71 (s, 1H), 7.56 (s, 1H), 7.40 (d, J = 8.0 Hz, 2H), 7.26 (d, J = 8.0 Hz, 2H), 7.18 (s, 1H), 6.93 (t, J = 3.2 Hz, 1H), 6.60 (d, J = 4.0 Hz, 1H), 4.28-4.20 (m, 1H), 4.15 (s, 2H), 4.03-4.0 (m, 2H), 3.93 (s, 3H), 3.87-3.83 (m, 1H), 3.66-3.62 (m, 1H), 3.58-3.50 (m, 1H), 2.36 (d, J = 8.8 Hz, 1H), 2.0-1.85 (m, 2H), 1.60-1.50 (m, 2H); Mass (m/z); 432.3 (M + H)$^+$. |

Example 39: N-[(1S,2S)-2-Hydroxycyclohexyl]-4-[4-(2-chloropyridin-4-yl)-benzyl]-pyrrolo[1,2-b]pyridazine-2-carboxamide

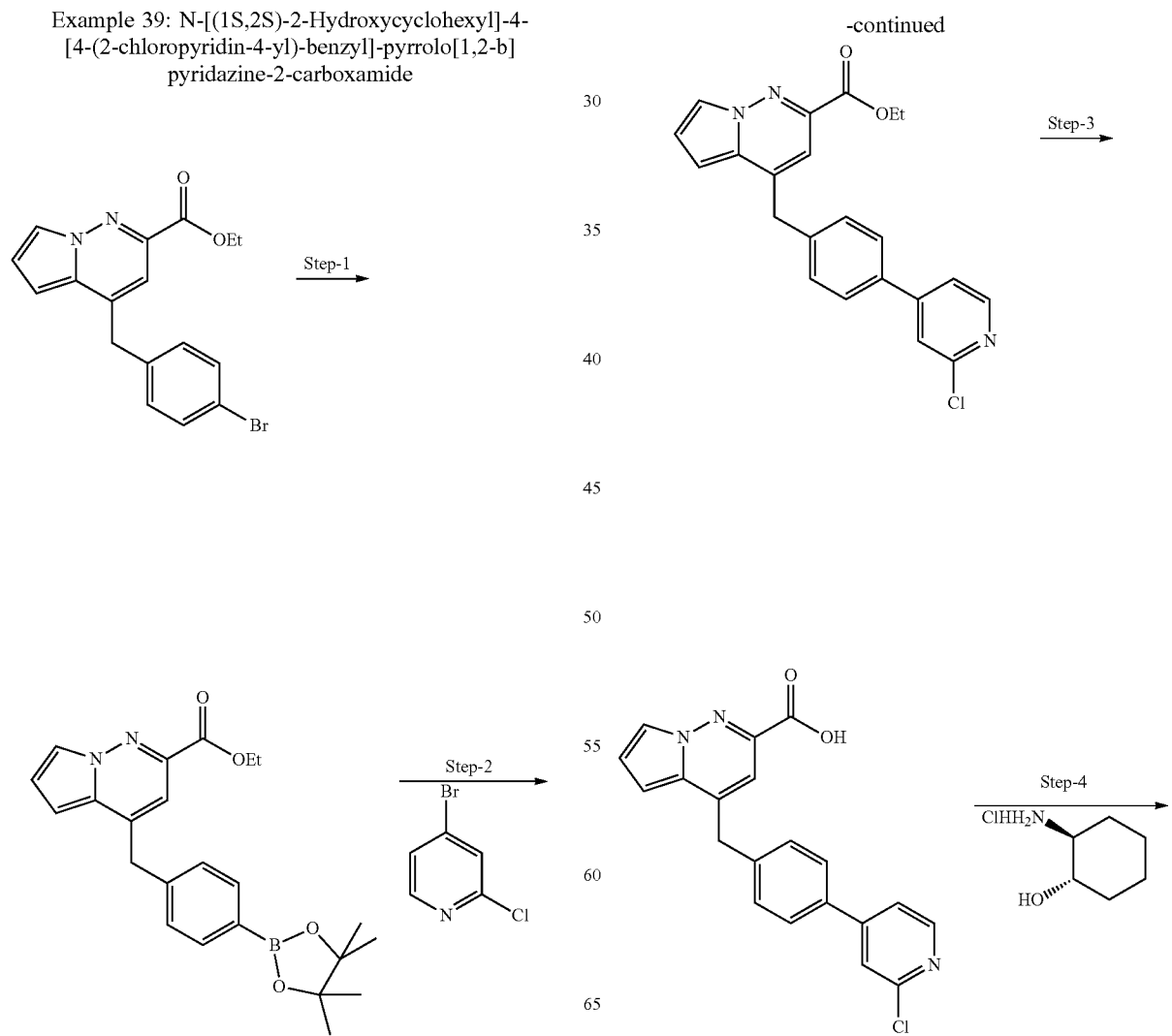

-continued

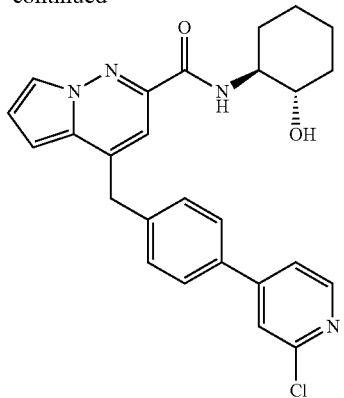

Step-1: To the stirred solution of step-2 product of example 19, ethyl 4-(4-bromobenzyl)-pyrrolo[1,2-b]pyridazine-2-carboxylate (2.0 g, 5.57 mmol) bis(pinacolato)diboran (2.12 g, 8.35 mmol) was added in presence of toluene (110.0 mL) at RT. The reaction mass was degassed for 5 minutes and $PdCl_2$ (dppf).$CH_2Cl_2$ (0.45 g, 0.55 mmol) was added. The reaction mixture temperature was raised to 110° C. and was stirred for 5 h. The reaction mixture was cooled to RT, and was filtered through a small pad of celite. The filtrate was evaporated under reduced pressure to obtain a crude mass which was purified by silica gel column chromatography to obtain step-1 compound ethyl 4-[4-(4,4,5,5-tetramethyl-[1,3,2]dioxaborolan-2-yl)-benzyl]pyrrolo[1,2-b]pyridazine-2-carboxylate (1.29 g) in 57% yield. $^1$H-NMR (400 MHz, $CDCl_3$): δ 7.89 (s, 1H), 7.76 (d, J=8.0 Hz, 2H), 7.28 (d, J=8.0 Hz, 2H), 7.01 (s, 1H), 6.94 (dd, J=2.0, 4.0 Hz, 1H), 6.57 (d, J=4.0 Hz, 1H), 4.50 (q, 2H), 4.17 (s, 2H), 1.43 (t, J=7.2 Hz, 3H), 1.33 (s, 12H); Mass (m/z); 407.1 $(M+H)^+$.

Step-2: To the stirred solution of step-1 product as obtained above, ethyl 4-(4-bromobenzyl)-pyrrolo[1,2-b]pyridazine-2-carboxylate (150 mg, 0.37 mmol) in 1,4-dioxan (3.7 mL), water (0.8 mL), potassium acetate (91.0 mg, 0.92 mmol) and 2-chloro-4-bromopyridine (85.0 mg, 0.44 mmol) were added. The reaction mass was degassed for 5 minutes and $PdCl_2$ (dppf).$CH_2Cl_2$ (30.0 mg, 0.04 mmol) was added. The reaction mixture temperature was raised to 100° C. and was stirred for 4 h. The reaction mixture was cooled to RT, and was filtered through a small pad of celite. The filtrate was evaporated under reduced pressure to obtain a crude mass which was purified by silica gel column chromatography to obtain step-2 compound ethyl 4-[4-(2-chloropyridin-4-yl)-benzyl]-pyrrolo[1,2-b]pyridazine-2-carboxylate (59.0 mg) in 41% yield. $^1$H-NMR (400 MHz, $CDCl_3$): δ8.40 (d, J=5.2 Hz, 1H), 7.92 (s, 1H), 7.76 (d, J=8.0 Hz, 2H), 7.52 (d, J=5.2 Hz, 1H), 7.44 (s, 1H), 7.44 (d, J=8.0 Hz, 2H), 7.06 (s, 1H), 6.99 (dd, J=1.8, 4.0 Hz, 1H), 6.61 (d, J=4.0 Hz, 1H), 4.51 (q, 2H), 4.23 (s, 2H), 1.43 (t, J=7.2 Hz, 3H); Mass (m/z); 392.0 $(M+H)^+$.

Step-3: To a stirred solution of ethyl 4-[4-(2-chloropyridin-4-yl)-benzyl]-pyrrolo[1,2-b]pyridazine-2-carboxylate as obtained in step-2 (59 mg, 0.15 mmol) in ethanol (2.0 mL) at RT, sodium hydroxide (12 mg, 0.3 mmol) dissolved in water (4.0 mL) was added. The reaction mixture was stirred at RT for 16 h. The reaction mass was diluted with water (10.0 mL) and extracted with ether to remove the non acidic impurities. The aqueous layer thus obtained was cooled to ice-bath temperature and was acidified with 1N HCl to pH 5. The aqueous layer was extracted with chloroform which was dried over anhydrous $Na_2SO_4$ and the solvent was removed under reduced pressure to obtain 4-[4-(2-chloro-pyridin-4-yl)-benzyl]-pyrrolo[1,2-b]pyridazine-2-carboxylic acid (0.041 g) in 75% yield. $^1$H-NMR (400 MHz, $CDCl_3$): δ8.43 (d, J=5.4 Hz, 1H), 7.85 (s, 1H), 7.59 (d, J=7.9 Hz, 2H), 7.51 (s, 1H), 7.45 (d, J=7.9 Hz, 2H), 7.43 (d, J=5.4 Hz, 1H), 7.12 (s, 1H), 7.07 (s, 1H), 7.04 (dd, J=1.9, 3.9 Hz, 1H), 6.71 (d, J=3.9 Hz, 1H), 4.26 (s, 2H); Mass (m/z); 364.0 $(M+H)^+$.

Step-4: To a solution of 4-[4-(2-chloropyridin-4-yl)-benzyl]-pyrrolo[1,2-b]pyridazine-2-carboxylic acid (41.0 mg, 0.11 mmol) in DCM (5.0 mL) at 0 to 5° C. under $N_2$, DIPEA (0.04 mL, 0.23 mmol), TBTU (40.0 mg, 0.12 mmol) and 1-amino-2-hydroxy-cyclohexane (13.0 mg, 0.11 mmol) were added sequentially. The reaction mass was gradually warmed to r.t., and was stirred for 4 h. The reaction mixture was quenched with ice water (5.0 mL) and was extracted with DCM (10 mL×2). Organic layer was washed with brine solution (50 mL), dried over anhydrous $Na_2SO_4$ and the solvent was evaporated under reduced pressure to obtain the crude compound which was purified by flash chromatography using to afford the title compound N-[(1 S,2S)-2-Hydroxycyclohexyl]-4-[4-(2-chloropyridin-4-yl)-benzyl]-pyrrolo[1,2b]pyridazine-2-carboxamide (29.0 mg) in 56% yield. $^1$H-NMR (400 MHz, $CDCl_3$): δ 8.43 (d, J 5.2 Hz, 1H), 7.75 (s, 1H), 7.56 (d, J=7.9 Hz, 2H), 7.51 (s, 1H), 7.40 (d, J 7.9 Hz, 2H), 7.40 (d, J 5.2 Hz, 1H), 7.19 (s, 1H), 6.95 (dd, J 1.9, 4.0 Hz, 1H), 6.60 (d, J 4.0 Hz, 1H), 4.22 (s, 2H), 3.88-3.78 (m, 1H), 3.55-3.46 (m, 1H), 3.02 (d, J 4.4 Hz, 1H), 2.18-2.07 (m, 2H), 1.85-1.75 (m, 2H), 1.45-1.25 (in, 4H); Mass (m/z); 461.1 $(M+H)^+$.

Examples 40 to 50: The compounds of Example 40 to Example 50 were prepared by following the experimental procedures as described in the Example 39, with some non-critical variations.

| Example No. | Structure and IUPAC name | Characterization data |
|---|---|---|
| Example 40 | 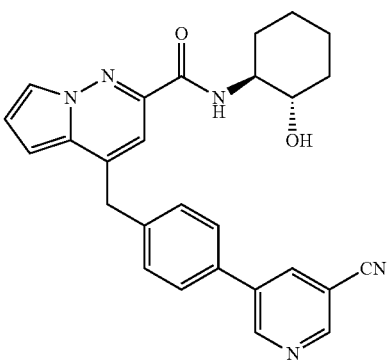<br>N-[(1S,2S)-2-Hydroxycyclohexyl]-4-[4-(5-cyanopyridin-3-yl)-benzyl]-pyrrolo[1,2-b]pyridazine-2-carboxamide | $^1$H - NMR (400 MHz, CDCl$_3$): δ9.00 (s, 1H), 8.83 (s, 1H), 8.09 (s, 1H), 7.76 (s, 1H), 7.52 (d, J = 8.0 Hz, 2H), 7.44 (d, J = 8.0 Hz, 2H), 7.20 (s, 1H), 6.95 (t, J = 3.6 Hz, 1H), 6.61 (d, J = 3.6 Hz, 1H), 4.23 (s, 2H), 3.88-3.77 (m, 1H), 3.55-3.46 (m, 1H), 2.95 (bs, 1H), 2.16-2.06 (m, 2H), 1.83-1.73 (m, 2H), 1.48-1.25 (m, 4H); Mass (m/z); 452.2 (M + H)$^+$. |
| Example 41 | 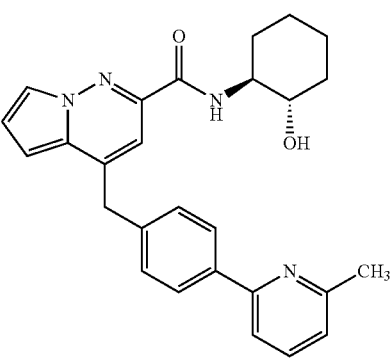<br>N-[(1S,2S)-2-Hydroxycyclohexyl]-4-[4-(6-methylpyridin-2-yl)-benzyl]-pyrrolo[1,2-b]pyridazine-2-carboxamide | $^1$H - NMR (400 MHz, CDCl$_3$): δ7.92 (d, J = 8.0 Hz, 2H), 7.89 (s, 1H), 7.60 (t, J = 8.0 Hz, 2H), 7.48 (d, J = 8.0 Hz, 1H), 7.44 (d, J = 7.2 Hz, 1H), 7.36 (d, J = 8.0 Hz, 2H), 7.22 (s, 1H), 7.08 (d, J = 7.6 Hz, 1H), 6.92 (t, J = 3.6 Hz, 1H), 6.58 (d, J = 4.0 Hz, 1H), 4.21 (s, 2H), 3.88-3.78 (m, 1H), 3.55-3.46 (m, 1H), 3.10 (d, J = 4.4 Hz, 1H), 2.60 (s, 3H), 2.17-2.07 (m, 2H), 1.82-1.73 (m, 2H), 1.48-1.22 (m, 4H); Mass (m/z); 441.1 (M + H)$^+$. |
| Example 42 | 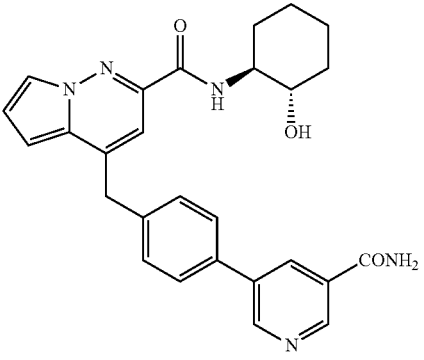<br>N-[(1S,2S)-2-Hydroxycyclohexyl]-4-[4-(5-carbamoylpyridin-3-yl)-benzyl]-pyrrolo[1,2-b]pyridazine-2-carboxamide | $^1$H - NMR (400 MHz, DMSO-d$_6$): δ9.0 (s, 1H), 8.97 (s, 1H), 8.44 (s, 1H), 8.22 (s, 1H), 8.21 (d, J = 8.4 Hz, 1H), 7.94 (s, 1H), 7.76 (d, J = 8.0 Hz, 2H), 7.64 (s, 1H), 7.54 (d, J = 8.0 Hz, 2H), 7.07 (s, 1H), 7.01 (t, J = 3.6 Hz, 1H), 6.84 (d, J = 4.0 Hz, 1H), 4.65 (d, J = 5.2 Hz, 1H), 4.30 (s, 2H), 3.64-3.53 (m, 1H), 3.50-3.40 (m, 1H), 1.92-1.82 (m, 2H), 1.68-1.58 (m, 2H), 1.40-1.18 (m, 4H); Mass (m/z); 470.2 (M + H)$^+$. |

-continued

| Example No. | Structure and IUPAC name | Characterization data |
|---|---|---|
| Example 43 | 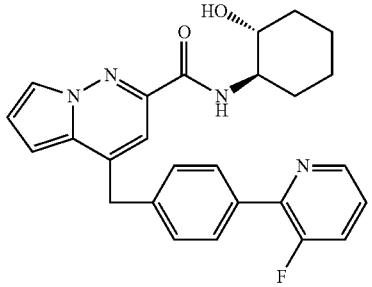<br>N-[(1S,2S)-2-Hydroxycyclohexyl]-4-[4-(6-fluoropyridin-2-yl)-benzyl]-pyrrolo[1,2-b]pyridazine-2-carboxamide | $^1$H - NMR (400 MHz, CDCl$_3$): δ 8.50 (d, J = 4.4 Hz, 1H), 7.93 (d, J = 7.6 Hz, 2H), 7.73 (s, 1H), 7.49-7.43 (m, 2H), 7.40 (d, J = 7.6 Hz, 2H), 7.30-7.22 (m, 2H), 6.93 (t, J = 6.8 Hz, 1H), 6.59 (d, J = 4 Hz, , 1H), 4.23 (s, 2H), 3.83-3.81 (m, 1H), 3.53-3.48 (m, 1H), 3.11 (d, J = 4.4 Hz, 1H), 2.14-2.08 (m, 2H), 1.78-1.77 (m, 2H), 1.48-1.38 (m, 4H); Mass (m/z); 445.2 (M + H)$^+$. |
| Example 44 | 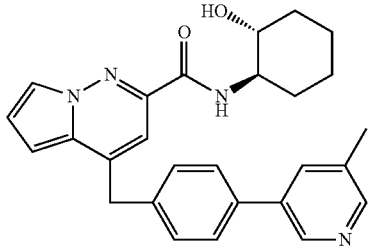<br>N-[(1S,2S)-2-Hydroxycyclohexyl]-4-[4-(5-methylpyridin-3-yl)-benzyl]-pyrrolo[1,2-b]pyridazine-2-carboxamide | $^1$H - NMR (400 MHz, CDCl$_3$): δ 8.62 (s, 1H), 8.40 (s, 1H), 7.75 (s, 1H), 7.64 (s, 1H), 7.51 (d, J = 8.4 Hz, 2H), 7.43 (d, J = 7.2 Hz, 1H), 7.38 (d, J = 8.4 Hz, 2H), 7.21 (s, 1H), 6.95 (t, J = 3.6 Hz, 1H), 6.62 (d, J = 4.0 Hz, 1H), 4.21 (s, 2H), 3.85-3.78 (m, 1H), 3.53-3.48 (m, 1H), 3.07 (d, J = 4.4 Hz, 1H), 2.39 (s, 3H), 2.14-2.08 (m, 2H), 1.78-1.76 (m, 1H), 1.46-1.28 (m, 4H); Mass (m/z); 441.0 (M + H)$^+$. |
| Example 45 | 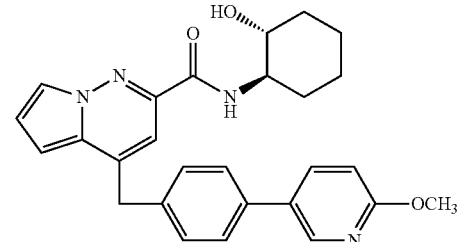<br>N-[(1S,2S)-2-Hydroxycyclohexyl]-4-[4-(4-methoxypyridin-3-yl)-benzyl]-pyrrolo[1,2-b]pyridazine-2-carboxamide | $^1$H - NMR (400 MHz, CDCl$_3$): δ 8.35 (d, J = 1.6 Hz, 1H), 7.79-7.72 (m, 2H), 7.46-7.44 (m, 2H), 7.35 (d, J = 8.0 Hz, 2H), 7.21 (s, 2H), 6.95 (t, J = 3.2 Hz, 1H), 6.81 (d, J = 8.4 Hz, 1H), 6.62 (d, J = 8.0 Hz, 1H), 4.20 (s, 2H), 3.97 (s, 3H), 3.83-3.81 (m, 1H), 3.53-3.49 (m, 1H), 3.06 (d, J = 4.4 Hz, 1H), 2.13-2.08 (m, 2H), 1.85-1.77 (m, 2H), 1.46-1.28 (m, 4H); Mass (m/z); 457.0 (M + H)$^+$. |
| Example 46 | 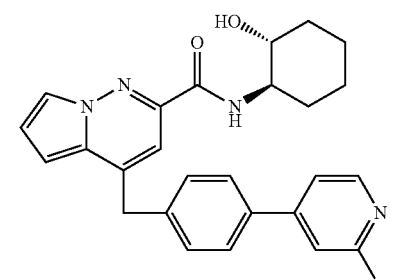<br>N-[(1S,2S)-2-Hydroxycyclohexyl]-4-[4-(3-methoxypyridin-4-yl)-benzyl]-pyrrolo[1,2-b]pyridazine-2-carboxamide | $^1$H - NMR (400 MHz, CDCl$_3$): δ 8.19 (d, J = 5.6 Hz, 1H), 7.75 (s, 1H), 7.55 (d, J = 8.0 Hz, 1H), 7.45 (d, J = 7.6 Hz, 1H), 7.38 (d, J = 8.0 Hz, 2H), 7.21 (s, 1H), 7.08 (dd, J = 6.8 Hz, 4.8 Hz, 1H), 6.95 (t, J = 3.6 Hz, 1H), 6.92 (s, 1H), 6.61 (d, J = 3.6 Hz, 1H), 4.21 (s, 2H), 3.97 (s, 3H), 3.83-3.81 (m, 1H), 3.49 (bs, 1H), 3.04 (bs, 1H), 2.14-2.08 (m, 2H), 1.80-1.71 (m, 2H), 1.45-1.35 (m, 4H); Mass (m/z); 457.1 (M + H)$^+$. |

| Example No. | Structure and IUPAC name | Characterization data |
|---|---|---|
| Example 47 | 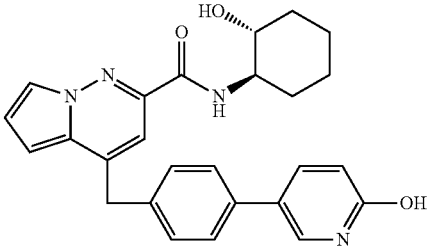<br>N-[(1S,2S)-2-Hydroxycyclohexyl]-4-[4-(4-hydroxypyridin-3-yl)-benzyl]-pyrrolo[1,2-b]pyridazine-2-carboxamide | $^1$H - NMR (400 MHz, CDCl$_3$): δ8.35 (d, J = 1.6 Hz, 1H), 7.77 (d, J = 7.2 Hz, 2H), 7.46-7.44 (m, 2H), 7.35 (d, J = 8.0 Hz, 2H), 7.21 (s, 2H), 6.95 (t, J = 3.2 Hz, 1H), 6.81 (d, J = 8.4 Hz, 1H), 6.62 (d, J = 8.0 Hz, 1H), 5.8 (bs, 1H), 4.20 (s, 2H), 3.83-3.81 (m, 1H), 3.53-3.49 (m, 1H), 3.06 (d, J = 4.4 Hz, 1H), 2.13-2.08 (m, 2H), 1.85-1.77 (m, 2H), 1.46-1.28 (m, 4H); Mass (m/z); 443.1 (M + H)$^+$. |
| Example 48 | 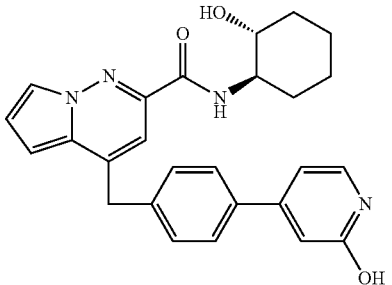<br>N-[(1S,2S)-2-Hydroxycyclohexyl]-4-[4-(3-hydroxypyridin-4-yl)-benzyl]-pyrrolo[1,2-b]pyridazine-2-carboxamide | $^1$H - NMR (400 MHz, CDCl$_3$): δ8.19 (d, J = 5.6 Hz, 1H), 7.75 (s, 1H), 7.55 (d, J = 8.0 Hz, 1H), 7.45 (d, J = 7.6 Hz, 1H), 7.38 (d, J = 8.4 Hz, 2H), 7.21 (s, 1H), 7.08 (dd, J = 6.8 Hz, 4.8 Hz, 1H), 6.95 (t, J = 3.6 Hz, 1H), 6.92 (s, 1H), 6.61 (d, J = 3.6 Hz, 1H), 5.71 (bs, 1H), 4.21 (s, 2H), 3.83-3.81 (m, 1H), 3.49 (bs, 1H), 3.04 (bs, 1H), 2.14-2.08 (m, 2H), 1.80-1.71 (m, 2H), 1.45-1.35 (m, 4H); Mass (m/z); 443.1 (M + H)$^+$. |
| Example 49 | 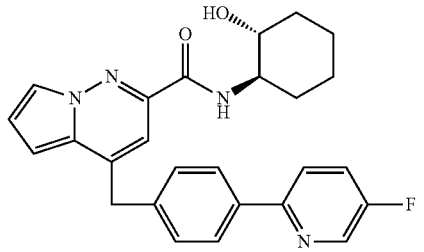<br>N-[(1S,2S)-2-Hydroxycyclohexyl]-4-[4-(4-fluoropyridin-2-yl)-benzyl]-pyrrolo[1,2-b]pyridazine-2-carboxamide | $^1$H - NMR (400 MHz, CDCl$_3$): δ8.51 (d, J = 2.4 Hz, 1H), 7.88 (d, J = 8.0 Hz, 2H), 7.74 (s, 1H), 7.70 (dd, J = 4.4, 8.8 Hz, 1H), 7.47-7.43 (m, 2H), 7.38 (d, J = 8.0 Hz, 2H), 7.25 (s, 1H), 6.93 (t, J = 3.2 Hz, 1H), 6.59 (d, J = 4.0 Hz, 1H), 4.21 (s, 2H), 3.83-3.81 (m, 1H), 3.52-3.49 (m, 1H), 3.08 (d, J = 3.6 Hz, 1H), 2.14-2.08 (m, 2H), 1.82-1.76 (m, 2H), 1.42-1.35 (m, 4H); Mass (m/z); 445.2 (M + H)$^+$. |
| Example 50 | 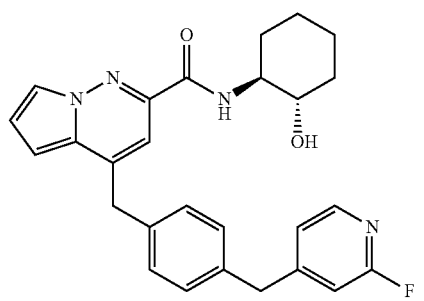<br>N-[(1S,2S)-2-Hydroxycyclohexyl]-4-[4-(2-fluoropyridin-4-yl-methyl)-benzyl]-pyrrolo[1,2-b]pyridazine-2-carboxamide | $^1$H - NMR (400 MHz, CDCl$_3$): δ8.09 (d, J = 5.2 Hz, 1H), 7.74 (s, 1H), 7.44 (d, J = 7.6 Hz, 1H), 7.24 (d, J = 8.0 Hz, 2H), 7.16 (s, 1H), 7.10 (d, J = 8.0 Hz, 2H), 6.98 (d, J = 5.2 Hz, 1H), 6.94 (t, J = 3.6 Hz, 1H), 6.70 (s, 1H), 6.59 (d, J = 3.2 Hz, 1H), 4.14 (s, 2H), 3.95 (s, 2H), 3.88-3.77 (m, 1H), 3.54-3.46 (m, 1H), 3.04 (d, J = 4.4 Hz, 1H), 2.18-2.07 (m, 2H), 1.82-1.75 (m, 2H), 1.48-1.22 (m, 4H); Mass (m/z); 459.1 (M + H)$^+$. |

Additional Examples:
The compounds of Example 51 to Example 71 were prepared by following the experimental procedures as described above, with some non-critical variations.

51  N-[(1S,2S)-2-Hydroxycyclohexyl]-4-(4-cyanobenzyl)-pyrrolo[1,2-b]pyridazine-2-carboxamide;
52  N-[(1S,2S)-2-Hydroxycyclohexyl]-4-(4-carbamoylbenzyl)-pyrrolo[1,2-b]pyridazine-2-carboxamide;
53  N-[(1S,2S)-2-Hydroxycyclohexyl]-4-(4-methylcarbamoylbenzyl)-pyrrolo[1,2-b]pyridazine-2-carboxamide;
54  N-[(1S,2S)-2-Hydroxycyclohexyl]-4-(4-ethylcarbamoylbenzyl)-pyrrolo[1,2-b]pyridazine-2-carboxamide
55  N-[(1S,2S)-2-Hydroxycyclohexyl]-4-(4-cyclopropylcarbamoylbenzyl)-pyrrolo[1,2-b]pyridazine-2-carboxamide
56  N-[(1S,2S)-2-Hydroxycyclohexyl]-4-(4-isopropylcarbamoylbenzyl)-pyrrolo[1,2-b]pyridazine-2-carboxamide
57  N-[(1S,2S)-2-Hydroxycyclohexyl]-4-(4-cyclopropylmethylcarbamoylbenzyl)-pyrrolo[1,2-b]pyridazine-2-carboxamide
58  N-[(1S,2S)-2-Hydroxycyclohexyl]-4-(4-isobutylcarbamoylbenzyl)-pyrrolo[1,2-b]pyridazine-2-carboxamide
59  N-[(1S,2S)-2-Hydroxycyclohexyl]-4-(3-methylcarbamoylbenzyl)-pyrrolo[1,2-b]pyridazine-2-carboxamide;
60  N-[(1S,2S)-2-Hydroxycyclohexyl]-4-(3-isobutylcarbamoylbenzyl)-pyrrolo[1,2-b]pyridazine-2-carboxamide
61  N-[(1S,2S)-2-Hydroxycyclohexyl]-4-(2-isobutylcarbamoylbenzyl)-pyrrolo[1,2-b]pyridazine-2-carboxamide
62  N-[(1S,2S)-2-Hydroxycyclohexyl]-4-[4-(4-cyanopyridin-2-yl)-benzyl]-pyrrolo[1,2-b]pyridazine-2-carboxamide
63  N-[(1S,2S)-2-Hydroxycyclohexyl]-4-[4-(4-carbamoylpyridin-2-yl)-benzyl]-pyrrolo[1,2-b]pyridazine-2-carboxamide
64  N-[(1S,2S)-2-Hydroxycyclohexyl]-4-[4-(4-methylcarbamoylpyridin-2-yl)-benzyl]-pyrrolo[1,2-b]pyridazine-2-carboxamide
65  N-[(1S,2S)-2-Hydroxycyclohexyl]-4-[4-(2-cyclopropylcarbamoylpyridin-5-yl)-benzyl]-pyrrolo[1,2-b]pyridazine-2-carboxamide
66  N-[(1S,2S)-2-Hydroxycyclohexyl]-4-[4-(5-cyclopropylcarbamoylpyridin-2-yl)-benzyl]-pyrrolo[1,2-b]pyridazine-2-carboxamide
67  N-[(1S,2S)-2-Hydroxycyclohexyl]-4-[4-(3-cyclopropylcarbamoylpyridin-4-yl)-benzyl]-pyrrolo[1,2-b]pyridazine-2-carboxamide
68  N-[(1S,2S)-2-Hydroxycyclohexyl]-4-[4-(4-methylcarbamoylphenyl)-benzyl]-pyrrolo[1,2-b]pyridazine-2-carboxamide
69  N-[(1S,2S)-2-Hydroxycyclohexyl]-4-[4-(4-methylcarbamoylphenyl)-pyridin-3-yl-methyl]-pyrrolo[1,2-b]pyridazine-2-carboxamide
70  N-[(1S,2S)-2-Hydroxycyclohexyl]-4-[4-(6-methylcarbamoylphenyl)-pyridin-3-yl-methyl]-pyrrolo[1,2-b]pyridazine-2-carboxamide
71  N-[(1S,2S)-2-Hydroxycyclohexyl]-4-[2-(4-methylcarbamoylphenyl)-pyridin-4-yl-methyl]-pyrrolo[1,2-b]pyridazine-2-carboxamide Example 72

Determination of Allosteric Potency $EC_{50}$ Values for Muscarinic M1 Receptor

A stable CHO cell line expressing recombinant human Muscarinic M1 receptor and pCRE-Luc reporter system was used for cell-based assay. The assay offers a non-radioactive based approach to determine binding of a compound to GPCRs. In this specific assay, the level of intracellular cyclic AMP which is modulated by activation or inhibition of the receptor is measured. The recombinant cells harbor luciferase reporter gene under the control of cyclic AMP response element.

The above cells were grown in 96 well clear bottom white plates in Hams F12 medium containing 10% fetal bovine serum (FBS). Prior to the addition of compounds or standard agonist, cells were serum starved overnight. Increasing concentrations of test compounds were added along with $EC_{20}$ of acetylcholine in OptiMEM medium to the cells. The incubation was continued at 37° C. in $CO_2$ incubator for 4 hours. Medium was removed and cells were washed with phosphate buffered saline. The cells were lysed and luciferase activity was measured in a Luminometer. Luminescence units were plotted against the compound concentrations using Graphpad software. $EC_{50}$ values of the compounds were defined as the concentration required in stimulating the luciferase activity by 50% in presence of $EC_{20}$ of acetylcholine and the results are provided in table 1.

TABLE 1

$EC_{50}$ values of the test compounds

| Example No. | $EC_{50}$ (nM) |
| --- | --- |
| Example 1 | 10000 |
| Example 2 | 555 |
| Example 3 | 941 |
| Example 4 | 1847 |
| Example 5 | 344 |
| Example 6 | 3991 |
| Example 7 | 847 |
| Example 8 | 10000 |
| Example 9 | 10000 |
| Example 10 | 10000 |
| Example 11 | 10000 |
| Example 12 | 1547 |
| Example 13 | 10000 |
| Example 14 | 976 |
| Example 15 | 10000 |
| Example 16 | 1004 |
| Example 17 | 1902 |
| Example 18 | 181 |
| Example 19 | 336 |
| Example 20 | 80 |
| Example 21 | 182 |
| Example 22 | 1664 |
| Example 23 | 1016 |
| Example 24 | 531 |
| Example 25 | 10000 |
| Example 26 | 75 |
| Example 27 | 133 |
| Example 28 | 586 |
| Example 29 | 1174 |
| Example 30 | 405 |
| Example 31 | 1547 |
| Example 32 | 2021 |
| Example 33 | 2109 |
| Example 34 | 2845 |
| Example 35 | 343 |
| Example 36 | 1152 |
| Example 37 | 411 |
| Example 38 | 692 |
| Example 39 | 224 |
| Example 40 | 146 |
| Example 41 | 41 |
| Example 42 | 36 |
| Example 43 | 701 |
| Example 44 | 96 |
| Example 45 | 108 |
| Example 46 | 118 |
| Example 49 | 149 |
| Example 50 | 518 |

Example 73

Rodent Pharmacokinetic Study

Male Wistar rats (260±50 grams) were used as experimental animals. Animals were housed individually in polypropylene cage. Two days prior to study, male Wistar rats were anesthetized with isoflurane for surgical placement of jugular vein catheter. Rats were randomly divided for oral (3 mg/kg) and intravenous (1 mg/kg) dosing (n=3/group) and fasted overnight before oral dosing (p.o.). However, rats allocated to intravenous dosing food and water was provided ad libitum.

At pre-determined point, blood was collected through jugular vein and replenished with an equivalent volume of normal saline. Collected blood was transferred into a labeled eppendorf tube containing 10 µL of heparin as an anticoagulant. Typically blood samples were collected at following time points: 0.08, 0.25, 0.5, 1, 2, 4, 6, 8, and 24 h post dose. Blood was centrifuged at 4000 rpm for 10 minutes. Plasma was separated and stored frozen at −80° C. until analysis. The concentrations of the test compounds were quantified in plasma by qualified LC-MS/MS method using suitable extraction technique. The test compounds were quantified in the calibration range around 1-1000 ng/mL in plasma. Study samples were analyzed using calibration samples in the batch and quality control samples spread across the batch.

Pharmacokinetic parameters $C_{max}$, $AUC_t$, $T_{1/2}$, Clearance and Bioavailability (F) were calculated by non-compartmental model using standard non-compartmental model by using Phoenix WinNonlin 6.0.4 version Software package.

TABLE 2

Pharmacokinetic profile of the test compounds

| Example No. | ROA | $C_{max}$ (ng/mL) | $AUC_{0-t}$ (ng · hr/mL) | $T_{1/2}$ (hr) | Clearance (mL/min/kg) | F (%) |
|---|---|---|---|---|---|---|
| Example 4 | oral (gavage) | 113 ± 11 | 259 ± 22 | 2.5 ± 0.5 | — | 13 ± 1 |
|  | intravenous (bolus) | — | 677 ± 194 | 0.7 ± 0.1 | 24 ± 6 |  |
| Example 14 | oral (gavage) | 68 ± 22 | 532 ± 102 | 7.9 ± 1.3 | — | 31 ± 6 |
|  | intravenous (bolus) | — | 569 ± 74 | 5.7 ± 0.7 | 27 ± 1 |  |
| Example 19 | oral (gavage) | 933 ± 260 | 1940 ± 520 | 1.0 ± 0.1 | — | 66 ± 18 |
|  | intravenous (bolus) | — | 983 ± 91 | 0.5 ± 0.0 | 17.0 ± 1.6 |  |
| Example 21 | oral (gavage) | 1064 ± 257 | 14233 ± 493 | 8.7 ± 3.0 | — | 58 ± 2 |
|  | intravenous (bolus) | — | 8197 ± 1558 | 8.1 ± 1.4 | 1.9 ± 0.5 |  |
| Example 24 | oral (gavage) | 16 ± 4 | 52 ± 8 | 1.9 ± 1.1 | — | 5 ± 1 |
|  | intravenous (bolus) | — | 359 ± 58 | 1.6 ± 0.3 | 47 ± 8 |  |
| Example 26 | oral (gavage) | 762 ± 80 | 2387 ± 129 | 1.77 ± 0.07 | — | 71 ± 4 |
|  | intravenous (bolus) | — | 1127 ± 61 | 1.8 ± 0.2 | 14.4 ± 1.0 |  |
| Example 27 | oral (gavage) | 397 ± 162 | 1001 ± 320 | 1.06 ± 0.08 | — | 49 ± 16 |
|  | intravenous (bolus) | — | 687 ± 50 | 1.1 ± 0.3 | 24 ± 1.8 |  |
| Example 29 | oral (gavage) | 1813 ± 327 | 6027 ± 279 | 2.2 ± 0.6 | — | 88 ± 4 |
|  | intravenous (bolus) | — | 2280 ± 161 | 1.5 ± 0.1 | 7.2 ± 0.5 |  |
| Example 31 | oral (gavage) | 363 ± 40 | 1963 ± 360 | 2.8 ± 0.1 | — | 114 ± 20 |
|  | intravenous (bolus) | — | 576 ± 192 | 1.5 ± 0.4 | 30.3 ± 8.9 |  |
| Example 38 | oral (gavage) | 1857 ± 185 | 13000 ± 954 | 3.74 ± 0.15 | — | 60 ± 4 |
|  | intravenous (bolus) | — | 7240 ± 890 | 3.42 ± 0.29 | 2.31 ± 0.29 |  |
| Example 44 | oral (gavage) | 1437 ± 241 | 4427 ± 618 | 1.79 ± 0.37 | — | 64 ± 9 |
|  | intravenous (bolus) | — | 2293 ± 121 | 1.7 ± 0.1 | 7.1 ± 0.4 |  |
| Example 45 | oral (gavage) | 202 ± 21.2 | 617 ± 193 | 1.8 ± 0.1 | — | 26 ± 8 |
|  | intravenous (bolus) | — | 786 ± 149 | 1.7 ± 0.2 | 21.3 ± 4.0 |  |
| Example 46 | oral (gavage) | 392 ± 60 | 803 ± 67 | 2.4 ± 1.1 | — | 38 ± 3 |
|  | intravenous (bolus) | — | 707 ± 52 | 2.3 ± 0.4 | 22.4 ± 1.7 |  |

Example 74

Rodent Brain Penetration Study

Male Wistar rats (260±40 grams) were used as experimental animals. Three animals were housed in each cage. Animals were given water and food ad libitum throughout the experiment and maintained on a 12 h light/dark cycle.

Brain penetration was determined in discrete manner in rats. One day prior to dosing day, male Wistar rats were acclimatized and randomly grouped according to their weight. At each time point (0.50, 1 and 2 h) n=3 animals were used.

The test compounds were suitably preformulated and administered orally at (free base equivalent) 3 mg/kg. Blood samples were removed via cardiac puncture by using isoflurane anesthesia. The animals were sacrificed to collect brain tissue. Plasma was separated and brain samples were homogenized and stored frozen at −20° C. until analysis.

The concentrations of the test compounds in plasma and brain were determined using LC-MS/MS method.

The test compounds were quantified in plasma and brain homogenate by qualified LC-MS/MS method using suitable extraction technique. The test compounds were quantified in the calibration range of 1-500 ng/mL in plasma and brain homogenate. Study samples were analyzed using calibration samples in the batch and quality control samples spread across the batch. Extent of brain-plasma ratio (Cb/Cp) was calculated.

TABLE 3

Blood Brain Penetration data of the test compounds

| Example No. | Single dose Rat Brain Penetration (Cb/Cp) at 3 mg/kg, p.o. |
| --- | --- |
| Example 4 | 1.42 ± 0.1 |
| Example 14 | 3.26 ± 0.02 |
| Example 19 | 0.26 ± 0.02 |
| Example 21 | 0.47 ± 0.04 |
| Example 24 | 0.38 ± 0.0 |
| Example 26 | 0.63 ± 0.07 |
| Example 27 | 0.63 ± 0.05 |
| Example 29 | 0.31 ± 0.04 |
| Example 31 | 1.41 ± 0.19 |
| Example 38 | 0.15 ± 0.02 |
| Example 44 | 0.17 ± 0.01 |
| Example 45 | 0.73 ± 0.14 |
| Example 46 | 1.75 ± 0.24 |

Example 75

Object Recognition Task Model

Male Wistar rats (8-10 weeks old) were used as experimental animals. Four animals were housed in each cage. Animals were kept on 20% food deprivation from a day prior to experimentation. Water was provided ad libitum throughout the experiment. Animals were maintained on a 12 h light/dark cycle in temperature and humidity controlled room. The experiment was carried out in a circular or square arena made up of acrylic. Rats were habituated to individual arenas for up to 1 hour in the absence of any objects on day 1.

One group of 12 rats received vehicle and another set of animals received test compounds, before familiar ($T_1$) and choice ($T_2$) trials. During the familiarization phase, ($T_1$), the rats were placed individually in the arena for 3 minutes, in which two identical objects ($a_1$ and $a_2$) were positioned 10 cm from the wall. 24 h after $T_1$, trial for long-term memory test was performed. The same rats were placed in the same arena as they were placed in $T_1$ trial. During the choice phase ($T_2$) rats were allowed to explore the arena for 3 minutes in presence of a copy of familiar object ($a_3$) and one novel object (b). During the $T_1$ and $T_2$ trial, explorations of each object (defined as sniffing, licking, chewing or having moving vibrissae whilst directing the nose towards the object at a distance of less than 1 cm) were recorded using stopwatch.

$T_1$ is the total time spent exploring the familiar objects ($a_1+a_2$).

$T_2$ is the total time spent exploring the familiar object and novel object ($a_3+b$).

The object recognition test was performed as described in *Behav. Brain Res.*, 1988, 31, 47-59.

TABLE 4

Novel objection recognition data of test compounds

| Example No. | Dose | Exploration time mean ± S.E.M (sec) | | Inference |
| --- | --- | --- | --- | --- |
| | | Familiar object | Novel object | |
| Example 4 | 3 mg/kg, p.o. | 16.24 ± 1.09 | 25.9 ± 2.54 | Active |
| Example 14 | 3 mg/kg, p.o. | 11.28 ± 2.18 | 23.08 ± 2.96 | Active |
| Example 29 | 1 mg/kg, p.o. | 12.17 ± 1.26 | 22.26 ± 1.05 | Active |
| Example 31 | 0.1 mg/kg, p.o. | 14.19 ± 1.02 | 20.18 ± 1.21 | Active |

Example 76

Object Recognition Task Model (Combination Study)

The cognition enhancing properties of compounds of this invention were estimated by using this model.

Male Wistar rats (8-10 weeks old) were used as experimental animals. Four animals were housed in each cage. Animals were kept on 20% food deprivation from a day prior to experimentation. Water was provided ad libitum throughout the experiment. Animals were maintained on a 12 h light/dark cycle in temperature and humidity controlled room. The experiment was carried out in an open field made up of acrylic. Rats were habituated to individual arenas (open field) for 20 minutes in the absence of any objects on day 1.

One group of 12 rats received vehicle and another set of animals received compound of the formula (I) or Donepezil or compound of formula (I) and Donepezil, before the familiar ($T_1$) and choice ($T_2$) trials. During the familiarization phase, ($T_1$), the rats were placed individually in the arena for 3 minutes, in which two identical objects ($a_1$ and $a_2$) were positioned 10 cm from the wall. 24 h after $T_1$, trial for long-term memory test was performed.

The same rats were placed in the same arena as they were placed in $T_1$ trial. During the choice phase ($T_2$) rats were allowed to explore the arena for 3 minutes in presence of a copy of familiar object ($a_3$) and one novel object (b). During the $T_1$ and $T_2$ trial, explorations of each object (defined as sniffing, licking, chewing or having moving vibrissae whilst directing the nose towards the object at a distance of less than 1 cm) were recorded using stopwatch.

$T_1$ is the total time spent exploring the familiar objects ($a_1+a_2$).

$T_2$ is the total time spent exploring the familiar object and novel object ($a_3+b$).

Discriminative index=Time spent with novel object/(time spent with novel and familiar object).

The object recognition test was performed as described by in *Behav. Brain Res.*, 1988, 31, 47-59.

Procognitive effects were observed with combination of sub efficacious doses of Example 4 and donepezil. The results of this study are provided in FIG. 1.

Example 77

Effect on Colonic Transit

Male Swiss mice of body weight ~20-30 g were fasted for 16 hours with free access to water prior to the experiment. Mice were administrated example 1 or vehicle, 30 min after administration of 0.5 ml of carmine dye solution. Mice were sacrificed 3 hours after dye administration and the distance traveled by the dye from proximal colon was measured.

Colonic transit was expressed as % colonic transit=100× (length of colon in which carmine moved/total length of colon).

Results: The test compound (Example 38) at doses of 1 and 3 mg/kg, p.o. increased the colonic transit.

We claim:

1. A compound of formula (I),

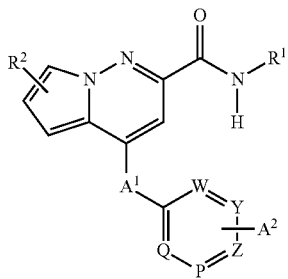

Wherein:
R¹ is selected from —(C₁₋₆)-alkyl, —(C₅₋₇)-cycloalkyl, —(C₅₋₇)-heterocycloalkyl, or —(C₆₋₁₀)-aryl; each of which is optionally substituted with one or more groups selected from halogen, hydroxy, NH₂, CH₂OH or (C₁₋₄)-alkyl;
A¹ is CH₂, CHF or CF₂;
P is CH, or N;
Q is CH, or N;
W is CH, or N;
Y is CH, or N;
Z is CH, or N;
A² is selected from hydrogen, halogen, —OR², —NHR², —NHCOR², —CN, —CONHR², —CON(R²)₂, —(C₁₋₄)-alkyl, —(C₃₋₆)-cycloalkyl, (C₆₋₁₀)-aryl and/or —(C₅₋₁₀)-heteroaryl; wherein each of the —(C₁₋₄)-alkyl, —(C₃₋₆)-cycloalkyl, —(C₆₋₁₀)-aryl and —(C₅₋₁₀)-heteroaryl is optionally substituted with one or more substituents independently selected from halogen, —OR², —O—(C₁₋₄)-alkyl, —S—(C₁₋₄)-alkyl, —N(CH₃)₂, —(C₁₋₄)-alkyl, —(C₃₋₆)-cycloalkyl, halo (C₁₋₄)-alkyl, —NHR², —CN, —CONHR₂, —NHCOR², or —CON(R²)₂;
each R², is independently selected from hydrogen, halogen, —(C₁₋₆)-alkyl, —(C₃₋₆)-cycloalkyl or halo(C₁₋₄)-alkyl;
or an isotopic form, a stereoisomer, a tautomer or a pharmaceutically acceptable salt thereof.

2. The compound as claimed in claim 1, wherein the compound is selected from the group consisting of:
N-[1-Hydroxy-cyclohexylmethyl]4-(4-chlorobenzyl)-pyrrolo[1,2-b]pyridazine-2-carboxamide;
N-[(1S,2S)-2-Hydroxycyclohexyl]-4-(4-chlorobenzyl)-pyrrolo[1,2-b]pyridazine-2-carboxamide;
N-[2-Hydroxy-2-methyl-propyl]-4-(4-chlorobenzyl)-pyrrolo[1,2-b]pyridazine-2-carboxamide;
N-[(1S,2S)-2-Hydroxycyclohexyl]-4-benzyl-pyrrolo[1,2-b]pyridazine-2-carboxamide;
N-[(1S,2S)-2-Hydroxycyclohexyl]-4-(4-bromobenzyl)-pyrrolo[1,2-b]pyridazine-2-carboxamide;
N-[(4-Hydroxy-tetrahydro-pyran-4-ylmethyl)]-4-(4-chlorobenzyl)-pyrrolo[1,2-b]pyridazine-2-carboxamide;
N-[(1S,2S)-2-Hydroxycyclohexyl]-4-(3-fluorobenzyl)-pyrrolo[1,2-b]pyridazine-2-carboxamide;
N-[Cyclohexyl]-4-(4-chlorobenzyl)-pyrrolo[1,2-b]pyridazine-2-carboxamide;
N-[Cyclopentyl]-4-(4-chlorobenzyl)-pyrrolo[1,2-b]pyridazine-2-carboxamide;
N-[Cyclohexyl]-4-(4-bromobenzyl)-pyrrolo[1,2-b]pyridazine-2-carboxamide;
N-[Cyclopentyl]-4-(4-bromobenzyl)-pyrrolo[1,2-b]pyridazine-2-carboxamide;
N-[2-hydroxyethyl]-4-(4-bromobenzyl)-pyrrolo[1,2-b]pyridazine-2-carboxamide;
N-[tetrahydrofuran-3-yl]-4-(3-fluorobenzyl)-pyrrolo[1,2-b]pyridazine-2-carboxamide;
N-[Tetrahydropyran-4-yl]-4-(4-chlorobenzyl)-pyrrolo[1,2-b]pyridazine-2-carboxamide;
N-[2-hydroxyphenyl]-4-(4-bromobenzyl)-pyrrolo[1,2-b]pyridazine-2-carboxamide;
N-[1-Hydroxymethyl-propyl]-4-(4-bromobenzyl)-pyrrolo[1,2-b]pyridazine-2-carboxamide;
N-[1-Hydroxymethyl-2-methylpropyl]-4-(4-bromobenzyl)-pyrrolo[1,2-b]pyridazine-2-carboxamide;
N-[Tetrahydrofuran-2-yl-methyl]-4-(4-bromobenzyl)-pyrrolo[1,2-b]pyridazine-2-carboxamide;
N-[2-hydroxy-2-methyl-propyl]4-[4-(1-methyl-1H-pyrazol-4-yl)-benzyl]-pyrrolo[1,2-b]pyridazine-2-carboxamide;
N-[(1S,2S)-2-Hydroxy-cyclohexyl]4-[4-(1-methyl-1H-pyrazol-4-yl)-benzyl]-pyrrolo[1,2-b]pyridazine-2-carboxamide;
N-[Tetrahydropyran-4-yl]4-[4-(1-methyl-1H-pyrazol-4-yl)-benzyl]-pyrrolo[1,2-b]pyridazine-2-carboxamide;
N-[4-Hydroxy-tetrahydro-pyran-4-ylmethyl]4-[4-(1-methyl-1H-pyrazol-4-yl)-benzyl]-pyrrolo[1,2-b]pyridazine-2-carboxamide;
N-[(1S,2S)-2-Hydroxycyclohexyl]4-[4-(4-fluorophenyl)-benzyl]-pyrrolo[1,2-b]pyridazine-2-carboxamide;
N-[1-Hydroxy-cyclohexylmethyl]4-[4-(1-methyl-1H-pyrazol-4-yl)-benzyl]-pyrrolo[1,2-b]pyridazine-2-carboxamide;
N-[(1S,2S)-2-Hydroxycyclohexyl]4-[4-(2-methoxyphenyl)-benzyl]-pyrrolo[1,2-b]pyridazine-2-carboxamide;
N-[(1S,2S)-2-Hydroxycyclohexyl]4-[4-(3-pyridyl)-benzyl]-pyrrolo[1,2-b]pyridazine-2-carboxamide;
N-[(1S,2S)-2-Hydroxycyclohexyl]4-[4-(4-pyridyl)-benzyl]-pyrrolo[1,2-b]pyridazine-2-carboxamide;
N-[Tetrahydropyran-4-yl]4-[4-(3-pyridyl)-benzyl]-pyrrolo[1,2-b]pyridazine-2-carboxamide;
N-[2-Hydroxy-2-methyl-propyl]4-[4-(3-pyridyl)-benzyl]-pyrrolo[1,2-b]pyridazine-2-carboxamide;
N-[2-Hydroxy-2-methyl-propyl]4-[4-(4-pyridyl)-benzyl]-pyrrolo[1,2-b]pyridazine-2-carboxamide;
N-[Tetrahydropyran-4-yl]4-[4-(4-pyridyl)-benzyl]-pyrrolo[1,2-b]pyridazine-2-carboxamide;
N-[Tetrahydrofuran-3-yl]4-[4-(1-methyl-1H-pyrazol-4-yl)-benzyl]-pyrrolo[1,2-b]pyridazine-2-carboxamide;
N-[Tetrahydrofuran-3-yl]4-[4-(4-pyridyl)-benzyl]-pyrrolo[1,2-b]pyridazine-2-carboxamide;
N-[Tetrahydrofuran-3-yl]4-[4-(3-pyridyl)-benzyl]-pyrrolo[1,2-b]pyridazine-2-carboxamide;
N-[Tetrahydrofuran-3-ylmethyl]4-[4-(1-methyl-1H-pyrazol-4-yl)-benzyl]-pyrrolo[1,2-b]pyridazine-2-carboxamide;
N-[1-Hydroxymethyl-propyl]4-[4-(1-methyl-1H-pyrazol-4-yl)-benzyl]-pyrrolo[1,2-b]pyridazine-2-carboxamide;
N-[1-Hydroxymethyl-2-methylpropyl]4-[4-(1-methyl-1H-pyrazol-4-yl)-benzyl]-pyrrolo[1,2-b]pyridazine-2-carboxamide;

N-[3-Hydroxy-tetrahydropyran-4-yl]4-[4-(1-methyl-1H-pyrazol-4-yl)-benzyl]-pyrrolo[1,2-b]pyridazine-2-carboxamide;
N-[(1S,2S)-2-Hydroxycyclohexyl]-4-[4-(2-chloropyridin-4-yl)-benzyl]-pyrrolo[1,2-b]pyridazine-2-carboxamide;
N-[(1S,2S)-2-Hydroxycyclohexyl]-4-[4-(5-cyanopyridin-3-yl)-benzyl]-pyrrolo[1,2-b]pyridazine-2-carboxamide;
N-[(1S,2S)-2-Hydroxycyclohexyl]-4-[4-(6-methylpyridin-2-yl)-benzyl]-pyrrolo[1,2-b]pyridazine-2-carboxamide;
N-[(1S,2S)-2-Hydroxycyclohexyl]-4-[4-(5-carbamoylpyridin-3-yl)-benzyl]-pyrrolo[1,2-b]pyridazine-2-carboxamide;
N-[(1S,2S)-2-Hydroxycyclohexyl]-4-[4-(6-fluoropyridin-2-yl)-benzyl]-pyrrolo[1,2-b]pyridazine-2-carboxamide;
N-[(1S,2S)-2-Hydroxycyclohexyl]-4-[4-(5-methylpyridin-3-yl)-benzyl]-pyrrolo[1,2-b]pyridazine-2-carboxamide;
N-[(1S,2S)-2-Hydroxycyclohexyl]-4-[4-(4-methoxypyridin-3-yl)-benzyl]-pyrrolo[1,2-b]pyridazine-2-carboxamide;
N-[(1S,2S)-2-Hydroxycyclohexyl]-4-[4-(3-methoxypyridin-4-yl)-benzyl]-pyrrolo[1,2-b]pyridazine-2-carboxamide;
N-[(1S,2S)-2-Hydroxycyclohexyl]-4-[4-(4-hydroxypyridin-3-yl)-benzyl]-pyrrolo[1,2-b]pyridazine-2-carboxamide;
N-[(1S,2S)-2-Hydroxycyclohexyl]-4-[4-(3-hydroxypyridin-4-yl)-benzyl]-pyrrolo[1,2-b]pyridazine-2-carboxamide;
N-[(1S,2S)-2-Hydroxycyclohexyl]-4-[4-(4-fluoropyridin-2-yl)-benzyl]-pyrrolo[1,2-b]pyridazine-2-carboxamide;
N-[(1S,2S)-2-Hydroxycyclohexyl]-4-[4-(2-fluoropyridin-4-yl-methyl)-benzyl]-pyrrolo[1,2-b]pyridazine-2-carboxamide;
N-[(1S,2S)-2-Hydroxycyclohexyl]-4-(4-cyanobenzyl)-pyrrolo[1,2-b]pyridazine-2-carboxamide;
N-[(1S,2S)-2-Hydroxycyclohexyl]-4-(4-carbamoylbenzyl)-pyrrolo[1,2-b]pyridazine-2-carboxamide;
N-[(1S,2S)-2-Hydroxycyclohexyl]-4-(4-methylcarbamoylbenzyl)-pyrrolo[1,2-b]pyridazine-2-carboxamide;
N-[(1S,2S)-2-Hydroxycyclohexyl]-4-(4-ethylcarbamoylbenzyl)-pyrrolo[1,2-b]pyridazine-2-carboxamide;
N-[(1S,2S)-2-Hydroxycyclohexyl]-4-(4-cyclopropylcarbamoylbenzyl)-pyrrolo[1,2-b]pyridazine-2-carboxamide;
N-[(1S,2S)-2-Hydroxycyclohexyl]-4-(4-isopropylcarbamoylbenzyl)-pyrrolo[1,2-b]pyridazine-2-carboxamide;
N-[(1S,2S)-2-Hydroxycyclohexyl]-4-(4-cyclopropylmethylcarbamoylbenzyl)-pyrrolo[1,2-b]pyridazine-2-carboxamide;
N-[(1S,2S)-2-Hydroxycyclohexyl]-4-(4-isobutylcarbamoylbenzyl)-pyrrolo[1,2-b]pyridazine-2-carboxamide;
N-[(1S,2S)-2-Hydroxycyclohexyl]-4-(3-methylcarbamoylbenzyl)-pyrrolo[1,2-b]pyridazine-2-carboxamide;
N-[(1S,2S)-2-Hydroxycyclohexyl]-4-(3-isobutylcarbamoylbenzyl)-pyrrolo[1,2-b]pyridazine-2-carboxamide;
N-[(1S,2S)-2-Hydroxycyclohexyl]-4-(2-isobutylcarbamoylbenzyl)-pyrrolo[1,2-b]pyridazine-2-carboxamide;
N-[(1S,2S)-2-Hydroxycyclohexyl]-4-[4-(4-cyanopyridin-2-yl)-benzyl]-pyrrolo[1,2-b]pyridazine-2-carboxamide;
N-[(1S,2S)-2-Hydroxycyclohexyl]-4-[4-(4-carbamoylpyridin-2-yl)-benzyl]-pyrrolo[1,2-b]pyridazine-2-carboxamide;
N-[(1S,2S)-2-Hydroxycyclohexyl]-4-[4-(4-methylcarbamoylpyridin-2-yl)-benzyl]-pyrrolo[1,2-b]pyridazine-2-carboxamide;
N-[(1S,2S)-2-Hydroxycyclohexyl]-4-[4-(2-cyclopropylcarbamoylpyridin-5-yl)-benzyl]-pyrrolo[1,2-b]pyridazine-2-carboxamide;
N-[(1S,2S)-2-Hydroxycyclohexyl]-4-[4-(5-cyclopropylcarbamoylpyridin-2-yl)-benzyl]-pyrrolo[1,2-b]pyridazine-2-carboxamide;
N-[(1S,2S)-2-Hydroxycyclohexyl]-4-[4-(3-cyclopropylcarbamoylpyridin-4-yl)-benzyl]-pyrrolo[1,2-b]pyridazine-2-carboxamide;
N-[(1S,2S)-2-Hydroxycyclohexyl]-4-[4-(4-methylcarbamoylphenyl)-benzyl]-pyrrolo[1,2-b]pyridazine-2-carboxamide;
N-[(1S,2S)-2-Hydroxycyclohexyl]-4-[4-(4-methylcarbamoylphenyl)-pyridin-3-yl-methyl]-pyrrolo[1,2-b]pyridazine-2-carboxamide;
N-[(1S,2S)-2-Hydroxycyclohexyl]-4-[4-(6-methylcarbamoylphenyl)-pyridin-3-yl-methyl]-pyrrolo[1,2-b]pyridazine-2-carboxamide; and
N-[(1S,2S)-2-Hydroxycyclohexyl]-4-[2-(4-methylcarbamoylphenyl)-pyridin-4-yl-methyl]-pyrrolo[1,2-b]pyridazine-2-carboxamide;
or a pharmaceutically acceptable salt thereof.

3. A pharmaceutical composition comprising a compound of formula (I) or a pharmaceutically acceptable salt thereof, as claimed in claim 1, and pharmaceutically acceptable excipients for the treatment of disease or disorder mediated by muscarinic M1 receptor, wherein said disease or disorder is selected from the group consisting of cognitive disorders, pain, sleep disorder and gastrointestinal motility disorders.

4. A combination comprising a compound as claimed in claim 1 and one or more therapeutic agents selected from acetylcholinesterase inhibitors and NMDA receptor antagonists.

5. The combination as claimed in claim 4, wherein the acetylcholinesterase inhibitor is selected from the group consisting of galantamine, rivastigmine, donepezil and tacrine, or a pharmaceutically acceptable salt thereof and NMDA receptor antagonist is memantine or a pharmaceutically acceptable salt thereof.

6. A method of treating a disease or disorder mediated by muscarinic M1 receptor, wherein the disease or disorder is selected from the group consisting of cognitive disorders, pain, sleep disorder and gastrointestinal motility disorders comprising administering to a patient in need of such treatment, a therapeutically effective amount of a compound of formula (I) or a pharmaceutically acceptable salt thereof as claimed in claim 1.

7. The method of treating a disease or disorder as claimed in claim 6, wherein the cognitive disorder is selected from the group consisting of dementia in Alzheimer's disease, dementia in Parkinson's disease, dementia in Huntington's disease, dementia associated with Down syndrome, dementia associated with Tourette's syndrome, dementia associated with post menopause, frontotemporal dementia, Lewy body dementia, vascular dementia, dementia in HIV, dementia in Creutzfeldt-Jakob disease, substance-induced persisting dementia, dementia in Pick's disease, dementia in schizophrenia and senile dementia.

8. A pharmaceutical composition comprising a compound of formula (I) or a pharmaceutically acceptable salt thereof, as claimed in claim 2, and pharmaceutically acceptable excipients for the treatment of disease or disorder mediated by muscarinic M1 receptor, wherein said disease or disorder is selected from the group consisting of cognitive disorders, pain, sleep disorder and gastrointestinal motility disorders.

9. A combination comprising a compound as claimed in claim 2 and one or more therapeutic agents selected from acetylcholinesterase inhibitors and NMDA receptor antagonists.

10. The combination as claimed in claim 9, wherein the acetylcholinesterase inhibitor is selected from the group consisting of galantamine, rivastigmine, donepezil and tacrine, or a pharmaceutically acceptable salt thereof and NMDA receptor antagonist is memantine or a pharmaceutically acceptable salt thereof.

11. A method of treating a disease or disorder mediated by muscarinic M1 receptor, wherein the disease or disorder is selected from the group consisting of cognitive disorders, pain, sleep disorder and gastrointestinal motility disorders comprising administering to a patient in need of such treatment, a therapeutically effective amount of a compound of formula (I) or a pharmaceutically acceptable salt thereof as claimed in claim 2.

12. The method of treating a disease or disorder as claimed in claim 11, wherein the cognitive disorder is selected from the group consisting of dementia in Alzheimer's disease, dementia in Parkinson's disease, dementia in Huntington's disease, dementia associated with Down syndrome, dementia associated with Tourette's syndrome, dementia associated with post menopause, frontotemporal dementia, Lewy body dementia, vascular dementia, dementia in HIV, dementia in Creutzfeldt-Jakob disease, substance-induced persisting dementia, dementia in Pick's disease, dementia in schizophrenia, and senile dementia.

* * * * *

UNITED STATES PATENT AND TRADEMARK OFFICE
CERTIFICATE OF CORRECTION

| | | |
|---|---|---|
| PATENT NO. | : 12,122,779 B2 | Page 1 of 1 |
| APPLICATION NO. | : 17/285432 | |
| DATED | : October 22, 2024 | |
| INVENTOR(S) | : Nirogi et al. | |

It is certified that error appears in the above-identified patent and that said Letters Patent is hereby corrected as shown below:

In the Specification

In Column 3, Line 18, please delete "$CONHR_2$" and add --$CONHR^2$--;
Line 19, please delete "aryland" and add --aryl and--;
Line 21, please delete "aryland" and add --aryl and--.

In the Claims

In Claim 1, Column 61, Line 38, please delete "and/or" and add --or--;
Line 45, please delete "$CONHR_2$" and add --$CONHR^2$--.

Signed and Sealed this
Eighteenth Day of February, 2025

Coke Morgan Stewart
*Acting Director of the United States Patent and Trademark Office*